United States Patent [19]

Collins et al.

[11] Patent Number: 4,997,929

[45] Date of Patent: Mar. 5, 1991

[54] PURIFIED CILIARY NEUROTROPHIC FACTOR

[75] Inventors: Franklin D. Collins; Leu-Fen Lin, both of Boulder, Colo.

[73] Assignee: Synergen, Inc., Boulder, Colo.

[21] Appl. No.: 404,533

[22] Filed: Sep. 8, 1989

Related U.S. Application Data

[63] Continuation-in-part of Ser. No. 293,851, Jan. 5, 1989.

[51] Int. Cl.$^5$ .................... C12P 21/00; C12N 15/00; C07H 15/12
[52] U.S. Cl. .................... 536/27; 435/240.2; 435/69.4; 435/69.1; 935/13; 935/70
[58] Field of Search .................... 435/69.1, 69.4, 172.3, 435/240.2, 320; 935/70, 60; 530/412, 417, 418, 419; 536/27

[56] References Cited

PUBLICATIONS

Collins, *Devel. Biol.*, vol. 109, pp. 255–258, 1985, "Electrophoretic Similarity of the Ciliary Ganglion Survival Factors from Different Tissues and Species".

Manthorpe et al., *Brain Res.*, vol. 367, pp. 282–286, 1986, "Purification of Adult Rat Sciatic Nerve Ciliary Neurotrophic Factor".

Hughes et al., *Nature,* vol. 335:70, 1988.

Ebendal, *Chem. Abst.*, vol. 106, No. 150248h, 1987, "Comparative Screening for Ciliary Neurotrophic Activity in Organs of the Rat and Chicken".

Lillien et al., Type-2 Astrocyte Development in Rat Brain Cultures is Initiated by a CNTF-like Protein Produced by Type-1 Astrocytes Neuron, vol. 1, 485–494, Aug. 1988.

*Primary Examiner*—Robin L. Teskin
*Attorney, Agent, or Firm*—Beaton & Swanson

[57] ABSTRACT

A ciliary neurotrophic factor (CNTF), particularly sciatic nerve CNTF(SN-CNFT) is claimed. The SN-CNTF described herein is a single protein species and has a specific activity that increased to greater than 25,000-fold from crude extract.

Amino acid data for this SN-CNTF is also provided. In addition, methods for using this data for providing SN-CNTF probes and for screening cDNA and genomic libraries are also provided. Recombinant-DNA methods for the production of SN-CNTF are described.

Nucleic acid sequences encoding rabbit and human CNTF are provided. A recombinant expression system is provided for producing biologically active CNTF.

3 Claims, 13 Drawing Sheets

FIG. 4
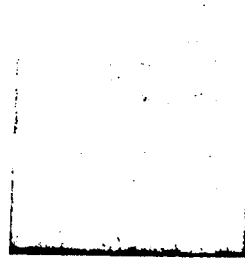
— 29K
— 20K
— 14K

FIG. 11

```
G CAA ACT CAG CTG ACT TGT TTC CTG GGA CAG TTG AGT TAG GGG ATG GCT
                                                                 M   A

TTC ATG GAG CAT TCA GCA CTG ACC CCT CAC CGC CGG GAG CTC TGT AGC
 F   M   E   H   S   A   L   T   P   H   R   R   E   L   C   S

CGT ACC ATC TGG CTA GCG AGG AAG ATT CGT TCA GAC CTG ACC GCT CTT
 R   T   I   W   L   A   R   K   I   R   S   D   L   T   A   L

ACG GAA TCT TAC GTG AAG CAT CAG GGC CTG AAC AAG AAC ATC AAC CTG
 T   E   S   Y   V   K   H   Q   G   L   N   K   N   I   N   L

GAC TCT GTG GAT GGA GTA CCA ATG GCA AGC ACT GAT CAG TGG AGT GAG
 D   S   V   D   G   V   P   M   A   S   T   D   Q   W   S   E

CTG ACT GAG GCA GAG CGA CTC CAA GAG AAC CTC CAA GCT TAT CGG ACC
 L   T   E   A   E   R   L   Q   E   N   L   Q   A   Y   R   T

TTC CAT ATT ATG TTG GCC AGG CTT TTA GAA GAC CAG CAG GTG CAT TTT
 F   H   I   M   L   A   R   L   L   E   D   Q   Q   V   H   F

ACC CCA GCT GAA GGT GAC TTC CAT CAA GCT ATA CAT ACC CTT TTA CTC
 T   P   A   E   G   D   F   H   Q   A   I   H   T   L   L   L

CAA GTT GCT GCC TTC GCT TAC CAG ATA GAG GAG TTA ATG GTG CTG TTG
 Q   V   A   A   F   A   Y   Q   I   E   E   L   M   V   L   L

GAA TGT AAT ATC CCT CCC AAA GAT GCT GAT GGG ACA CCT GTC ATT GGA
 E   C   N   I   P   P   K   D   A   D   G   T   P   V   I   S

GGT GAT GGT CTC TTT GAG AAG AAG CTG TGG GGC CTG AAG GTG CTA CAA
 B   D   S   L   F   E   K   K   L   W   S   L   K   V   L   Q

GAG CTT TCA CAC TGG ACA GTG AGA TCC ATT CAT GAC CTT CGT GTC ATT
 E   L   S   H   W   T   V   R   S   I   H   D   L   R   V   I

TCT TGT CAT CAA ACT GGA ATC CCA GCA CAT GGG AGC CAT TAT ATT GCT
 S   C   H   Q   T   G   I   P   A   H   G   S   H   Y   I   A

AAC GAC AAG GAA ATG TAG
 N   D   K   E   M
```

FIG. 12

```
                                              G                      TG
                                          TAA GGG ATG GCT TTC ACA GAG
                                              met ala phe thr glu
                                                                  met
      G A                          C        G          T A C
CAT TCA CCG CTG ACC CCT CAC CGT CGG GAC CTC TGT AGC CGC TCT ATC TGG
his ser pro leu thr pro his arg arg asp leu cys ser arg ser ile trp
        ala                             glu                 thr
   G                                      C                   T   C
CTA GCA AGG AAG ATT CGT TCA GAC CTG ACT GCT CTT ACG GAA TCC TAT GTG
leu ala arg lys ile arg ser asp leu thr ala leu thr glu ser tyr val T              A G A
AAG CAT CAG GGC CTG AAC AAG AAC ATC AAC CTG GAC TCT GCG GAT GGG ATG
lys his gln gly leu asn lyn asn ila asn leu asp ser ala asp gly met
                                                            val       val
     A                                      T
CCA GTG GCA AGC ACT GAT CAG TGG AGT GAG CTG ACC GAG GCA GAG CBA CTC
pro val ala ser thr asp gln trp ser glu leu thr glu ala glu arg leu
    met
         C                    G            A  A                      I
CAA GAG AAC CTT CAA GCT TAT CGT ACC TTC CAT GTT TTG TTG GCC AGG CTC
gln glu asn leu gln ala tyr arg thr phe his val leu leu ala arg leu
                                                  ile met
                                           G T
TTA GAA GAC CAG CAG GTG CAT TTT ACC CCA ACC GAA GGT GAC TTC CAT CAA
leu glu asp gln gln val his phe thr pro thr glu gly asp phe his gln
                                                ala
            T A.          T              C   T
GCT ATA CAT ACC CTT CTT CTC CAA GTC GCT GCC TTT GCA TAC CAG ATA GAG
ala ile his thr leu leu leu gln val ala ala phe ala tyr gln ile glu G G   G T         GT  T        T CC  A   T
GAG TTA ATG ATA CTC CTG GAA TAC AAG ATC CCC CGC AAT GAG GCT GAT GGG
glu leu met ile leu leu glu tyr lys ile pro arg asn glu ala asp gly
            val                 cys asn         pro lys asp
   CA    GC  ---          GT   A
ATG CCT ATT AAT GTT GGA GAT GGT GGT CTC TTT GAG AAG AAG CTG TGG GGC
met pro ile asn val gly asp gly gly leu phe glu lys lys leu trp gly
           val ---  ile     gly asp
 G            A    A                 C           G  A       T
CTA AAG GTG CTG CAG GAG CTT TCA CAG TGG ACA GTA AGG TCC ATC CAT GAC
leu lys val leu gln glu leu ser gln trp thr val arg ser ile his asp
                                 his
        G          G     A    A                         A
CTT CGT TTC ATT TCT TCT CAT CAG ACT GGG ATC CCA GCA CGT GGG ABC CAT
leu arg phe ile ser ser his gln thr gly ile pro ala arg gly ser his
        val         cys                                     his
                 G         G
TAT ATT GCT AAC AAC AAG AAA ATG TAG
tyr ile ala asn asn lys lys met
        asp         glu
```

PURIFIED CILIARY NEUROTROPHIC FACTOR

This application is a continuation-in-part application of U.S. patent application Ser. No. 07/293,851, filed Jan. 5, 1989, pending.

BACKGROUND OF THE INVENTION

The present invention relates to neurotrophic factors and ciliary neurotrophic factor (CNTF) in particular, as well as methods of purifying CNTF and producing recombinant CNTF.

Severe mental and physical disabilities result from the death of nerve or glial cells in the nervous system. The death of nerve or glial cells can be caused by neurodegenerative diseases such as Alzheimer's and Parkinson's diseases and multiple sclerosis, by the ischemia resulting from stroke, by a traumatic injury, or by the natural aging process.

Neurotrophic factors are a class of molecules that promote the survival and functional activity of nerve or glial cells. Evidence exists to suggest that neurotrophic factors will be useful as treatments to prevent nerve or glial cell death or malfunction resulting from the conditions enumerated above. Appel, 1981, *Ann. Neurology* 10:499.

The best characterized of such neurotrophic factors is nerve growth factor (NGF). NGF has been demonstrated to be a neurotrophic factor for the forebrain cholinergic nerve cells that die during Alzheimer's disease and with increasing age. The loss of these nerve cells is generally considered responsible for many of the cognitive deficits associated with Alzheimer's disease and with advanced age.

Experiments in animals demonstrate that NGF prevents the death of forebrain cholinergic nerve cells after traumatic injury and that NGF can reverse cognitive losses that occur with aging. Hefti and Weiner, 1986, *Ann. Neurology* 20:275; Fischer et al, 1987, *Nature*, 329:65. These results suggest the potential clinical utility in humans of this neurotrophic factor in the treatment of cognitive losses resulting from the death of forebrain cholinergic nerve cells through disease, injury or aging.

A complication of the use of neurotrophic factors is their specificity for only those subpopulations of nerve cells which possess the correct membrane receptors. Most nerve cells in the body lack NGF receptors and are apparently unresponsive to this neurotrophic factor. It is, therefore, of critical importance to discover new neurotrophic factors that can support the survival of different types of nerve or glial cells than does NGF.

New neurotrophic factors have been searched for by their ability to support the survival in culture of nerve cells that are not responsive to NGF. One widely used screening assay is designed to discover factors that promote the survival of ciliary ganglionic motor neurons that innervate skeletal and smooth muscle. These ciliary ganglionic nerve cells belong to the parasympathetic nervous system and their survival is not supported by NGF.

The presence of factors which promote the survival of ciliary ganglionic nerve cells have been reported from a variety of tissues and species. Many of these ciliary ganglionic neurotrophic activities have the following similar chemical and biological properties: (1) the activity is present in high concentration in sciatic nerves; (2) the neurotrophic activity survives exposure to the ionic detergent sodium dodecyl sulfate (SDS) and to the reducing agents beta-mercaptoethanol (BME) or dithiothreitol (DTT) during electrophoresis on SDS polyacrylamide reducing gels; and (3) on such gels the activity migrates with an apparent molecular weight between 24–28 kd. Collins, 1985, *Developmental Biology*, 109:255-258; Manthorpe et al., 1986, *Brain Research*, 367:282-286.

Based on these similar properties, it has been proposed that the same or closely related molecules, typically referred to as "ciliary neurotrophic factor" or "CNTF", are responsible for the ciliary ganglionic neurotrophic activities. Thus, the term CNTF is an operational definition referring to agents with the above properties that promote the survival of ciliary ganglionic nerve cells in culture. Without sufficient data to establish that the proteins responsible for these activities are identical, CNTFs will be distinguished by their tissue and species of origin. Thus, if the species of origin is rabbit, the nomenclature is rabbit sciatic nerve CNTF (rabbit SN-CNTF).

Sciatic nerve CNTF is apparently found in highest concentration in peripheral nerves, such as the sciatic nerve. It is released from cells in the nerve upon injury. SN-CNTF supports the survival and growth of all peripheral nervous system nerve cells tested, including sensory, sympathetic, and parasympathetic nerve cells. Thus, SN-CNTF has a broader range of responsive nerve cells than does NGF. A rat SN-CNTF has recently been shown to regulate the formation of specific types of glial cells in the central nervous system (Hughes et al., 1988, *Nature* 335:70).

The most reasonable hypothesis based on the evidence cited above is that sciatic nerve CNTF is a component of the response of the nervous system to injury. SN-CNTF released from cells in a damaged nerve would be expected to promote the survival and regrowth of injured nerve cells and regulate the functional activation of glial cells necessary for regeneration. These considerations indicate that SN-CNTF would have therapeutic value in reducing damage to the nervous system caused by disease or injury.

Despite widespread scientific interest in SN-CNTF, the difficulty of purifying substantial amounts from natural sources and the unavailability of human SN-CNTF have hampered attempts to demonstrate its value in sustaining the viability of nerve cells during disease or after injury. Prior attempts to purify a rat SN-CNTF has resulted in an 800-fold enrichment over crude nerve extract in terms of specific activity. Manthorpe et al., 1986, *Brain Research* 367:282-286.

However, an eight hundred-fold increase in specific activity was insufficient to produce a single protein species. Therefore, the product showing increased activity obtained from the method described by Manthorpe et al. is insufficient as it includes multiple protein species. It would be desirable to achieve a purification of SN-CNTF such that a single protein species is obtained with the appropriate biological activity. Once a single protein species is obtained, sequencing data obtained will be more accurate. By "single protein species," as that term is used hereafter in this specification and the appended claims, is meant a polypeptide or series of polypeptides with the same amino acid sequence throughout their active sites. In other words, if the operative portion of the amino acid sequence is the same between two or more polypeptides, they are "a single protein species" as defined herein even if there are minor heterogeneities with respect to length or charge.

SUMMARY OF INVENTION

An object of the present invention is to provide an improved method of purifying SN-CNTF.

Another object of the present invention is to provide a SN-CNTF purified to an extent greater than ever achieved before, such that a single protein species is obtained.

Yet another object of the present invention is to provide probes which facilitate screening of cDNA and genomic libraries in order to clone the animal and human genes encoding SN-CNTF.

Another object of the invention is to provide the nucleic acid and corresponding amino acid sequences for animal and human CNTF.

Another object of the invention is to provide recombinant expression systems in which the nucleic acid sequence for human or animal CNTF can be used to produce human or animal CNTF protein.

These and other objects are achieved by providing a method of purifying SN-CNTF such that specific activity is increased greater than 25,000-fold from crude extract to purified SN-CNTF. The SN-CNTF purified greater than 25,000-fold is also provided.

According to other preferred features of certain preferred embodiments of the present invention, SN-CNTF probes are provided for screening cDNA and genomic libraries for SN CNTF.

According to other preferred features of certain preferred embodiments of the present invention, rabbit and human amino acid and nucleic acid CNTF sequences are provided.

According to other preferred features of certain preferred embodiments of the present invention, a recombinant expression system is provided to produce biologically active animal or human CNTF.

According to other advantageous features of certain preferred embodiments of the present invention, a process of purifying SN-CNTF is provided which includes the steps of acid treatment, ammonium sulfate fractionation, chromatofocussing, running the preparation on SDS-Page gel and reverse phase-HPLC.

According to other preferred features of certain preferred embodiments of the present invention, additional purification steps are provided in which hydrophobic interaction chromatography is used immediately before and after chromatofocussing.

It is to be understood that both the foregoing general description and the following detailed description are exemplary and explanatory only, and are not restrictive of the invention, as claimed. The accompanying drawings, which are incorporated in and constitute a part of the specification, illustrate various embodiments of the invention and, together with the description, serve to explain the principles of the invention.

BRIEF DESCRIPTION OF THE DRAWINGS

FIG. 4 depicts exemplary results of a silver stained reducing SDS-Page gel run on fractions equivalent to those adjacent to and including the peak of neurotrophic activity shown in FIG. 3;

FIG. 11 depicts the nucleic acid sequence encoding for rabbit SN-CNTF. Translation of this nucleic acid sequence gives the corresponding amino acid sequence printed underneath in single letter code. Sequences that are underlined were confirmed by the amino acid sequence obtained from the SN-CNTF protein.

FIG. 12 depicts the nucleic acid and corresponding amino acid sequence (three letter code) for the coding sequence for human CNTF. The human sequences are between the lines. Where the rabbit nucleic acid or amino acid sequences differ from the human, they are written above and below the lines, respectively.

DESCRIPTION OF THE PREFERRED EMBODIMENTS

Figure 1:
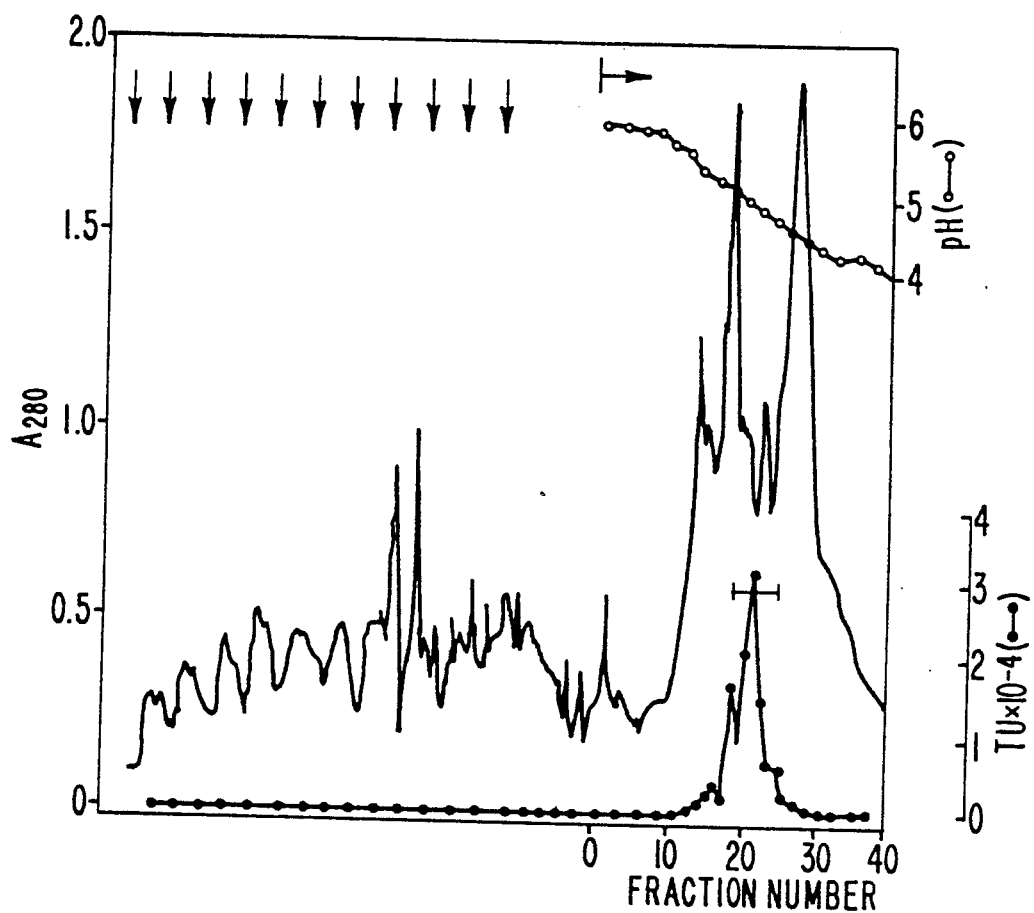
FIG. 1 depicts exemplary results of chromatography on a Mono P column.

Reference will now be made in detail to the presently preferred embodiments of the invention which, together with the following examples, serve to explain the principles of the invention.

As noted above, the present invention relates to an SN CNTF that is purified at least 25,000-fold from crude extract. This SN-CNTF is a single protein species as that term is defined herein. As a single protein species, the amino acid sequence of the SN-CNTF may be determined and used to design DNA probes for obtaining genomic or cDNA clones for use in recombinant production of SN-CNTF.

The amino acid sequence of the single protein species of SN-CNTF has been partially determined. That sequence is:

I—R—S—D—L—T—A—L—T—E—S—

Y—V—K—H—Q—G—L—N—K—N

D—G—V—P—M—A—G

K—L—W—G—L—K

Additional amino acid sequence has been determined from purified rabbit SN-CNTF which is given in Example 2. This additional sequence allows some of the amino acid sequence given above to be located within a single large peptide (Example 2). This single peptide sequence has been used to generate three degenerate oligonucleotide probes (#'s 1, 13, and 7 in Example 4) that are very useful for priming the polymerase chain reaction, since their position relative to each other is known.

The nucleic acid (mRNA equivalent) sequences encoding rabbit and human CNTF have been determined and are given in FIGS. 11 and 12.

A recombinant system for transiently expressing biologically active CNTF has been developed and is described in Example 5.

In addition, the present invention relates to an improved method of purifying SN-CNTF. While the present invention is related to SN-CNTF from any source, the description which follows will address that isolated from rabbits.

Briefly, one preferred embodiment of the present method includes pulverizing rabbit sciatic nerve material. The crude extract is then centrifuged. The supernatant is acidified and the resulting precipitate is removed by centrifugation. The supernatant is then titrated with NaOH and the resulting precipitate is again removed by centrifugation.

After pH precipitations, saturated ammonium sulfate solution is added to the supernatant and the precipitant is removed by centrifugation. With the further addition of ammonium sulfate to the supernatant, a precipitation of protein fraction containing most of the SN-CNTF activity results.

The above preparation is then loaded onto a Mono P chromatofocussing FPLC column. Column fractions are then collected and analyzed for pH and CNTF activity. The fractions indicated by a bar in FIG. 1 with peak SN-CNTF activity is then further treated as will be discussed in detail below.

The focused fractions from multiple runs over the Mono P column are electrophoresed on SDS polyacrylamide slab gel. A region of the gel corresponding to molecular weights between 22 and 27 kd is cut across the width of the gel into multiple strips. The individual strips are cut into smaller pieces and proteins are eluted electrophoretically. Eluted proteins are collected, and the fraction with the highest activity is further purified using reverse-phase HPLC. This process is described in more detail in the Examples which follow.

In addition, the present invention relates to additional steps that can be inserted into the purification procedure given above in order to allow more starting material to be processed conveniently. In a preferred embodiment of these additional steps, hydrophobic interaction chromatography on phenyl-Sepharose is inserted between ammonium sulfate fractionation and chromatofocussing, while hydrophobic interaction chromatography on an FPLC alkyl-Superose column is inserted between chromatofocussing and preparative SDS-PAGE (Example 1).

The method provided by the present invention has resulted in SN-CNTF in a purified form with a greater than 25,000-fold increase in specific activity from the crude extract. Further, the final product produced is a single protein species. This represents an increase of greater than 30-fold over the SN-CNTF, which includes multiple protein species, reported as purified in Manthorpe et al. discussed above. Since SN-CNTF is partially inactivated on reverse phase HPLC, the calculation of at least 25,000-fold purification according to the present invention represents a minimum purification, and the actual purification may be even 100,000-fold or greater. This increased purification will facilitate the determination of the amino acid sequence of SN-CNTF. According to the present invention, sufficient amino acid sequence has already been obtained to generate oligonucleotide probes that will facilitate screening of cDNA and genomic libraries in order to clone the animal and human genes coding for SN-CNTF.

The methods provided by the present invention have resulted in the determination of the coding (mRNA equivalent) sequence for rabbit and human CNTF.

As will be discussed in greater detail below, these genes will in turn make possible large-scale production of (1) animal SN-CNTF suitable for studies of its ability to treat animal models of nervous system damage, and (2) human SN-CNTF suitable for inclusion in pharmaceutical formulations useful in treating damage to the human nervous system.

The methods provided by the present invention have resulted in the production of biologically active animal CNTF in a recombinant expression system.

With these purified proteins, the amino acid sequence of the prominent peptides can be determined. The proteins are first treated with endoprotease Asp-N, endoprotease Lys-C, endoprotease Glu-C, or chymotrypsin. After digestion, the amino acid sequence of prominent peptides can be determined using an Applied Biosystems gas phase protein sequencer.

Figure 10A:
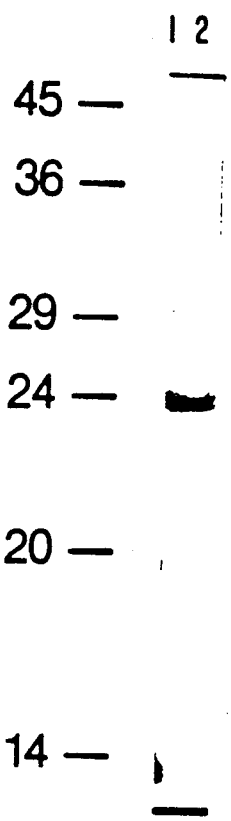
FIG. 10 depicts exemplary results of SDS-PAGE and Western blot analysis of the reverse-phase purified SN-CNTF. Lane 1 in each of the two panels contains molecular weight standard proteins (SIGMA SDS-7). Lane 2 contains purified SN-CNTF. Panel (A) illustrates the results of silver-staining. Panel (B) illustrates the results of Western blot analysis with affinity-purified anti-peptide-A antibody.
Figure 10B:

Antibodies that react with purified SN-CNTF can be used for screening expression libraries in order to obtain the gene which encodes SN-CNTF. Synthetic peptides can be synthesized which correspond to regions of the sequence of SN-CNTF using an Applied Biosystems automated protein synthesizer. Such peptides can be used to prepare the antibodies. Antibodies to synthetic peptides have been produced and shown to react with purified CNTF by Western blot analysis (FIG. 10).

From the work above, an ultimate goal is to clone and express the human SN-CNTF gene in order to prepare material suitable for use in human pharmaceutical preparations. Once the genomic sequence is known, genes encoding SN-CNTF can then be expressed in animal or bacterial cells. The rabbit and human gene sequences encoding CNTF have been determined. A transient expression system for producing biologically active CNTF has been developed.

The following examples are provided to illustrate certain preferred embodiments of the present invention, and are not restrictive of the invention, as claimed. All references provided in these Examples are specifically incorporated herein by reference.

EXAMPLE 1

Protein Preparation

Materials

Adult rabbit sciatic nerves were obtained from Pel-Freez Biologicals, Rogers, Ark. Ammonium sulfate (ultrapure) was purchased from Schwartz/Mann Biotech, Cleveland, Ohio. Phenylmethylsulfonyl fluoride (PMSF), epsilon-aminocaproic acid, benzamidine, pepstatin, dithiothreitol (DTT), poly-L ornithine (P3655), and 3-[4,5-dimethylthiazol-2 yl]-2,5-diphenyltetrazolium bromide (MTT) were obtained from Sigma Chemical Co., St. Louis, Mo. Mono P Chromatofocussing FPLC columns were obtained from Pharmacia, Inc., Piscataway, N.J. C8 reverse phase HPLC columns were obtained from Synchrom, Inc., Lafayette, Ind. Acetonitrile was purchased from J. T. Baker Chemical Co., Phillipsburg, N.J. Trifluoroacetic acid was obtained from Pierce Chemicals, Rockford, Ill. Endoproteases Asp-N and Lys-C were obtained from Boehringer Mannheim Biochemicals, Indianapolis, Ind. Fetal calf serum was purchased from Hyclone Laboratories, Logan, Utah. Culture media and salt solutions were obtained from Irvine Scientific, Santa Ana, Calif. Culture dishes were obtained from Costar, Cambridge, Mass. Utility grade pathogen-free fertile chick embryo eggs were obtained from Spafas, Roanoke, Ill.

B. Assay for SN-CNTF

Cultures of primary chick embryo ciliary ganglia were prepared as previously described (Collins, 1978, Develop. Biol. 65:50; Manthorpe et al., 1986, Develop. Brain Res. 25:191). Briefly, ciliary ganglia were removed from fertile, pathogen free chicken eggs that had been incubated for 9–10 days at 38° C. in a humidified atmosphere. The ganglia were chemically dissociated by exposure first to Hanks' Balanced Salt Solution without divalent cations, containing 10 mM HEPES buffer pH 7.2 for 10 min at 37° C., and then by exposure to a solution of 0.125% bactotrypsin 1:250 (Difco, Detroit, Mich.) in Hanks' Balanced Salt Solution modified as above for 12 min at 37° C. Trypsinization was stopped by addition of fetal calf serum to a final concentration of 10%.

After this treatment, ganglia were transferred to a solution consisting of Dulbecco's high glucose Modified Eagle Medium without bicarbonate containing 10% fetal calf serum and 10 mM HEPES, pH 7.2 and were mechanically dissociated by trituration approximately 10 times through a glass Pasteur pipet whose opening had been fire polished and constricted to a diameter such that it took 2 seconds to fill the pipet.

The dissociated ganglia were then plated in culture medium (Dulbecco's Modified Eagle Medium supplemented with 10% fetal calf serum, 4 mM glutamine, 60 mg/L penicillin-G, 25 mM HEPES, pH 7.2) in 100 mm diameter tissue culture dishes (40 dissociated ganglia per dish) for three hours. This preplating was done in order to separate the nonneuronal cells, which adhere to the dish, from the nerve cells, which do not adhere. After three hours, the nonadherent nerve cells were collected by centrifugation, resuspended in culture medium, and plated in 50 $\mu$l per well onto half area 96 well microtiter tissue culture plates at a density of 1500 nerve cells per well. The microtiter wells had been previously exposed to a 1 mg/ml solution of poly-L-ornithine in 10 mM sodium borate, pH 8.4 overnight at 4° C., washed in distilled water and air dried.

Ten $\mu$l of a serial dilution of the sample to be assayed for neurotrophic activity was added to each well and the dishes were incubated for 20 hours at 37° C. in a humidified atmosphere containing 7.5% $CO_2$. After 18 hours, 15 $\mu$l per well of a 1.5 mg/ml solution of the tetrazolium dye MTT in Dul Modified Eagle Medium without bicarbonate containing 10 mM HEPES, pH 7.2, was added and the cultures placed back in the 37° C. incubator for 4 hours. Then, 75 $\mu$l of a solution of 6.7 ml of 12M HCl per liter of isopropanol was added and the contents of each well triturated 30 times to break open the cells and suspend the dye. The absorbance at 570nm was determined relative to a 690nm reference for each well using an automatic microtiter plate reader (Dynatech, Chantilly, Va.). The absorbance of wells which had not received any neurotrophic agent (negative controls) was subtracted from the absorbance of sample-containing wells. The resulting absorbance is proportional to the number of living cells in each well, defined as those nerve cells capable of reducing the dye. The number of trophic units of neurotrophic activity was defined as the reciprocal of the dilution that gave 50% of maximal survival of nerve cells. The concentration of trophic activity in trophic units per ml was obtained by dividing the total trophic units by the assay volume (60 $\mu$l). Specific activity was determined by dividing the number of trophic units by the amount of protein present in the sample.

C. Purification of SN-CNTF

At the end of each of the following steps, the preparation was either processed immediately or stored at −70° C. for up to one week until used.

Step 1. Crude Extract Preparation

One Hundred grams (wet weight) of rabbit sciatic nerve (about 300 nerves) was thawed and pulverized using a Polytron rotary homogenizer (Kinematica, Switzerland) for 1 minute in 10 volumes (wt/vol) of water containing 10 mM EDTA, 1 mM epsilon aminocaproic acid, 1 mM benzamidine and, 0.1 mM PMSF, and centrifuged at 40,000$\times$g for 30 minutes at 4° C. The supernatant was filtered through glass wool to remove floating lipid.

Step 2. Acid Treatment and Ammonium Sulfate Fractionation

The centrifugation steps referred to below were performed at 17,000$\times$g for 20 minutes and all operations were performed at 4° C., unless otherwise stated. The crude extract was centrifuged. The supernatant was acidified to pH 3.6 with 5N HCl and the resulting precipitate was removed by centrifugation. The supernatant was titrated to pH 6.3 with 1N NaOH and the resulting precipitate was again removed by centrifugation. To the above supernatant was added saturated ammonium sulfate solution to achieve 30% saturation and the precipitate was removed by centrifugation. Further addition of ammonium sulfate to the supernatant to achieve 60% saturation resulted in the precipitation of a protein fraction containing most of the SN CNTF activity. The precipitate was dissolved in 20 mM sodium phosphate buffer, pH 6.7, containing 1 mM EDTA, 0.1 mM PMSF and 0.1 uM pepstatin, to give a protein concentration of 8–13 mg/ml.

Step 3. Chromatofocussing

The above preparation was dialyzed overnight against a 500 fold larger volume of 10 mM sodium phosphate, pH 6.7 with one change of buffer, and centrifuged at 140,000$\times$g for 30 minutes. The supernatant was passed through 0.22 $\mu$m pore-diameter nylon filter and loaded in 3 injections of 2 ml each onto a Mono P chromatofocussing FPLC column (bed volume 4 ml) equilibrated in 25 mM bis-Tris-HCl buffer, pH 5.8. The column was washed with same buffer until the absorbance at 280nm of the effluent returned to baseline. The sample was then chromatographed with polybuffer, pH 4.0 (1–10 dilution of PB74 from Pharmacia).

Column fractions were collected and analyzed for pH and CNTF activity. FIG. 1 shows the results of chromatography on Mono P. The profile of eluted proteins is plotted as the optical density (O.D.) at 280nm. Superimposed are plots of the pH and SN-CNTF activity measured in each fraction. The fractions indicated by the bar with peak SN-CNTF activity (around pH 5) were pooled and treated with solid ammonium sulfate to achieve 95% saturation and the pellet was collected by centrifugation, resuspended in saturated ammonium sulfate solution and centrifuged again to remove the polybuffer. The precipitate was dissolved in sufficient 10 mM sodium phosphate buffer, pH 6.7 to give a final protein concentration of 3-5 mg/ml (referred to as the "focused fraction"). Typically, 1 liter of the original crude extract was processed in 8 separate runs on the Mono P column.

Step 4. Preparative Sodium Dodecyl sulfate (SDS) Gel Electrophoresis

The focused fractions from multiple runs over the Mono P column were combined and dialyzed against a 100-fold larger volume of 10 mM sodium phosphate buffer, pH 6.7 for 8 hours with one change of buffer, then run on a 15% reducing SDS polyacrylamide slab gel according to the method of Laemmli, 1970. Each resolving gel measured 0.3 cm in thickness, 14 cm in height, and 11.5 cm in width. 5.5 mg of protein was loaded onto each gel. Electrophoresis was performed at 15° C. and 40 mA/gel until the 20 kd prestained molecular weight standard just reached the bottom of the resolving gel.

To reveal the curvature of individual protein bands across the width of the slab gel, the gel was overlayed with a sheet of nitrocellulose (0.45 um pore size in roll form obtained from Millipore Corporation, Bedford, Mass.) prewetted with water, 2 sheets of prewetted and 2 sheets of dry chromatography paper (3 MM Chr obtained from Whatman, Hillsboro, Oreg.), a glass plate and a 500 ml glass bottle for weight. After 30-45 minutes, the outline of the gel was traced onto the nitrocellulose paper using a water-insoluble marker. The paper was washed 3 times with 10 mm Tris-HCl buffer, pH 8.0 containing 0.15 M NaCl and 0.3% NP40 detergent, and then stained for 15-30 minutes with a 1:1000 dilution of Kohinuor Rapidograph Ink (available at stationary supply stores) in the above buffer.

Figure 2:
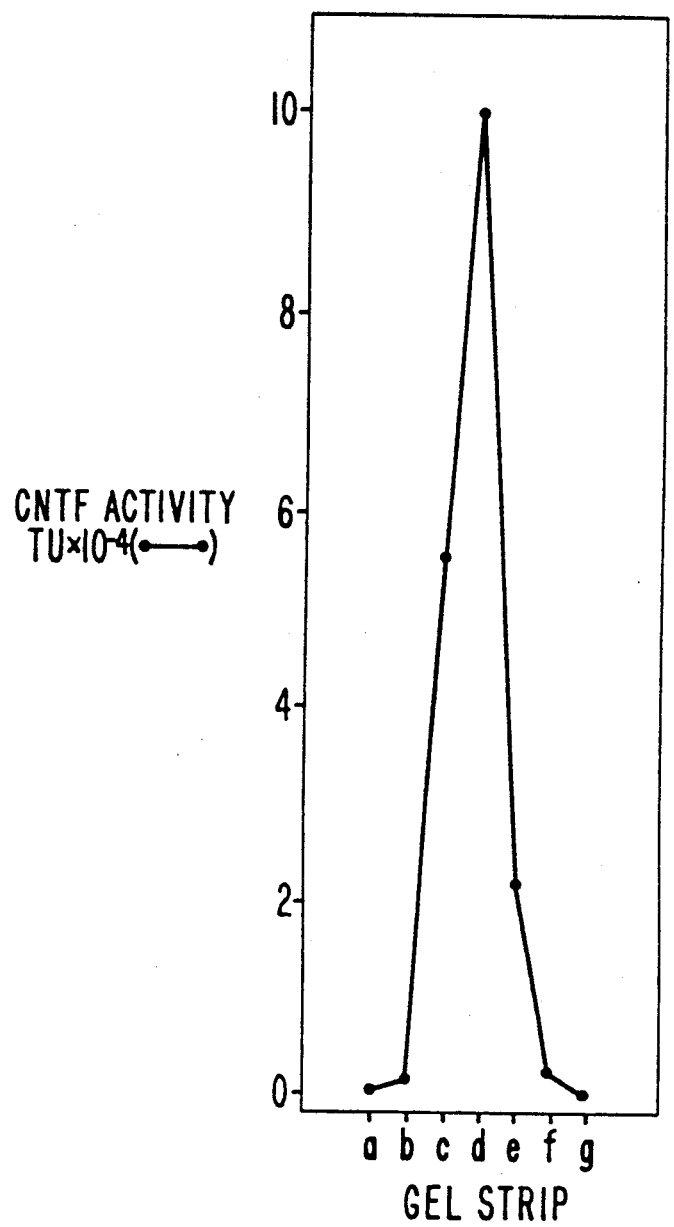
FIG. 2 depicts an exemplary plot of the distribution of neurotrophic activity in the elute from each of the seven strips cut from the SDS-Page gel after electrophoresis.

The original gel was placed onto a glass plate and aligned with its outline on the stained nitrocellulose paper underneath the glass. The region of the gel corresponding to molecular weights between 22-27 kd was located with reference to prestained molecular weight standards (BRL, Bethesda, Md.) run in narrow lanes at both ends of each gel. This region was cut across the width of the gel into seven 2.5 mm parallel strips using the banding curvature revealed by the stained nitrocellulose paper. Each individual gel strip was cut into smaller pieces (2.5×2 mm) and proteins were eluted electropohoretically for 6 hours in a 1:1 dilution of the Laemmli running buffer using an electrophoretic concentrator (ISCO, Lincoln, Nebr.). Eluted proteins were collected in a volume of 0.2 ml. FIG. 2 plots the distribution of neurotrophic activity in the elute from each of the 7 strips (labelled a-g in order of decreasing molecular weight). The fraction with the highest activity (strip d) was further purified using reverse-phase HPLC.

Step 5. Reverse Phase—HPLC

Figure 3:
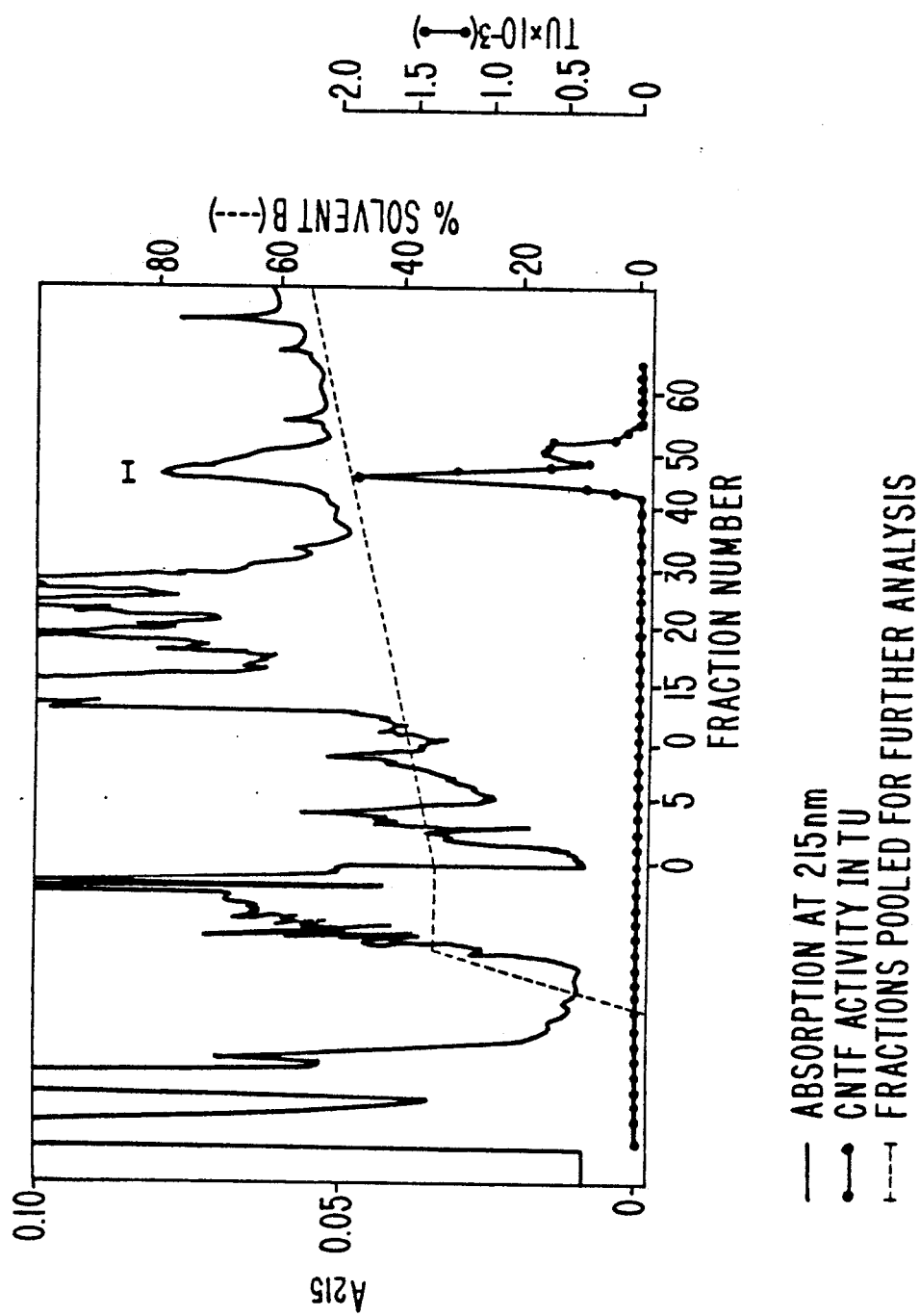
FIG. 3 depicts exemplary results of reverse phase chromatography.

Dithiothreitol (DTT) was and 10% trifluoracetic acid (TFA) were added to the gel eluate to achieve final concentrations of 2% and 0.3%, respectively. The sample was filtered through a 0.22 μm nylon filter, loaded onto a C8 reverse phase HPLC column and eluted with an $H_2O$/0.1% TFA:acetonitrile/0.1% TFA gradient Fractions were collected into siliconzied tubes containing 5 μl of 0.4% Tween 20 detergent. Aliquots from each fraction were assayed for neurotrophic activity. FIG. 3 shows the results of reverse phase chromatography. Protein concentration is indicated by absorbance at 215nm and the distribution of neurotrophic activity is superimposed. Fractions with the peak SN-CNTF activity (fractions 37-40, FIG. 3) were pooled for sequencing as described in Example 2. In a separate preparation, fractions adjacent to and including the peak CNTF activity, equivalent to fractions 36-44 in FIG. 3, were also analyzed on silver-stained reducing SDS-PAGE (FIG. 4).

Two additional chromatographic steps have also been performed. These steps confirmed the purity of the CNTF prepared above.

The two additional chromatographic steps both use the principle of hydrophobic interaction chromatography (HIC). The first HIC step is a conventional column chromatographic procedure inserted after step 2: pH and ammonium sulfate fractionation. The dissolved material after ammonium sulfate precipitation was further diluted with 10 mM sodium phosphate buffer, pH 6.7 (Buffer B) until the ionic strength (measured with a conductance meter) was equal to that of Buffer B containing 0.3M ammonium sulfate and 5% isopropanol (Buffer A). Isopropanol was then added to the diluted sample to a final concentration of 5% and the mixture applied to a column of phenyl Sepharose CL4B (Pharmacia, Inc., Piscataway, N.J.) equilibrated with Buffer A. No more than 3mg of sample protein was applied per ml of column bed-volume. Typically, 1 liter of crude sciatic nerve extract yielded 50ml. of the redissolved ammonium sulfate pellet, which was then diluted to 70-100ml as above and applied to a 110ml phenyl Sepharose column. The column was eluted stepwise starting with 3 bed-volumes of Buffer A, followed by 3 bed-volumes of Buffer B, followed by 2 bed-volumes of Buffer B containing 50% ethylene glycol (Buffer C), then washed with 5 bed-volumes of water. Eighteen ml fractions of the eluted material were collected.

Figure 7:
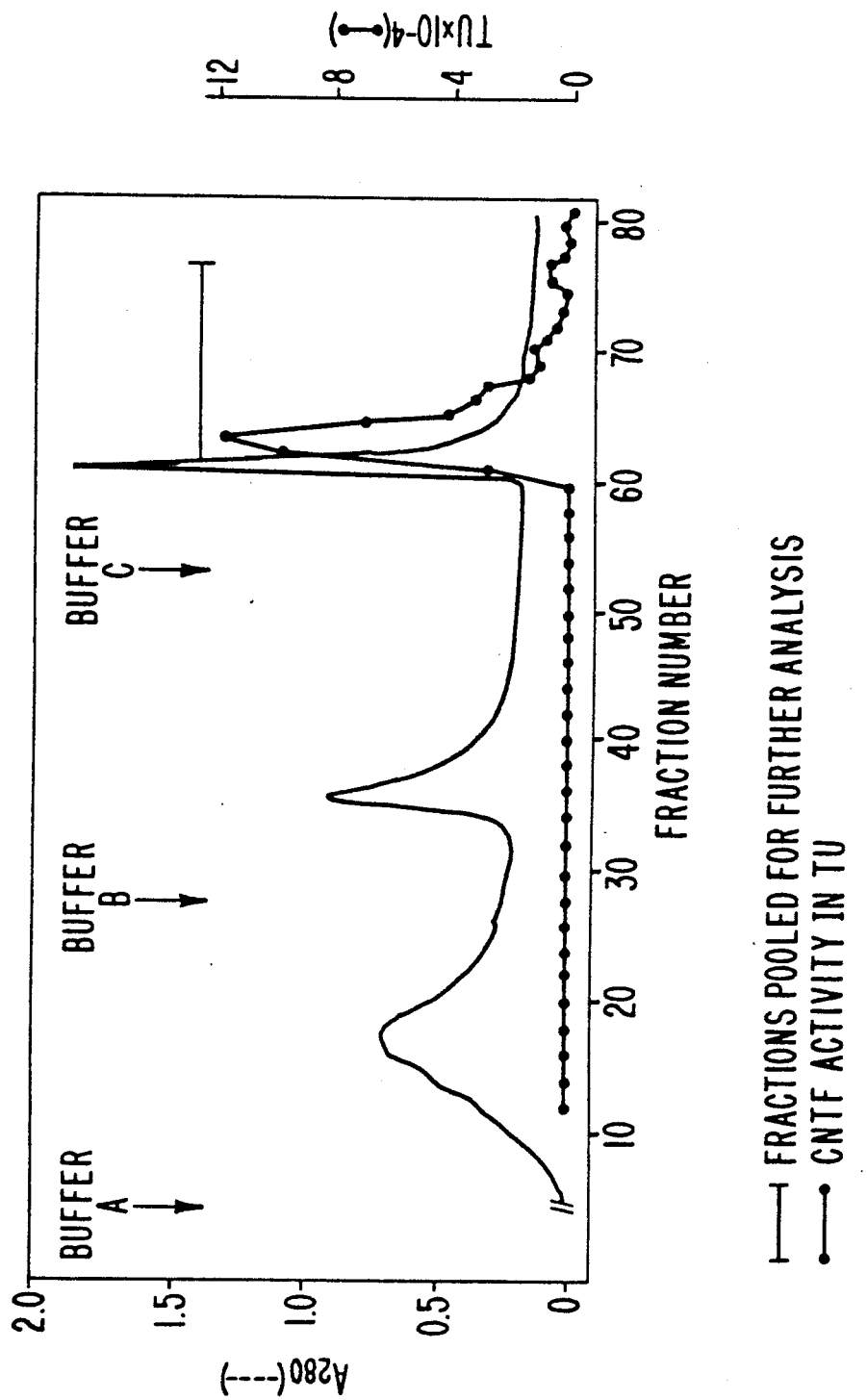
FIG. 7 depicts exemplary results of chromatography of the ammonium sulfate fraction on a phenyl Sepharose HIC column.

FIG. 7 shows the results of one such chromatography run. The profile of eluted proteins was continuously monitored by O.D. 280 (solid line). Superimposed on the O.D. tracing is the profile of eluted SN-CNTF bioactivity in each fraction (line connecting x's), as measured in the ciliary ganglion survival assay described in the original patent application. SN-CNTF bioactivity emerged from the column during elution with Buffer C. The column fractions containing the bulk of the bioactivity (indicated by the bar in FIG. 7) were pooled and concentrated by pressure dialysis using an Amicon YM-10 membrane (Amicon Division, W. R. Grace & Co., Danvers, Mass.) to approximately 1/10 of the original volume, which typically resulted in a final protein concentration of 2.5-3.0mg/ml. The concentrate was dialyzed for a total of 6hr against 3 changes of 55-fold larger volume of B. The dialyzed material was passed through a 0.2 μm pore diameter Acrodisc filter (Gelman Sciences, Inc., Ann Arbor, Mich.) and loaded in multiple injections of 2ml each onto a Mono-P chromatofocussing column as described in the original patent application.

Without this HIC column step, 1 liter of crude sciatic nerve extract required 8 separate runs on the Mono-P chromatofocussing column, as described in the initial patent application, because of the limited protein loading capacity of the column. With the addition of the HIC column step, 1 liter of crude extract could be processed in a single chromatofocussing run.

The second HIC step was inserted after the original step 3: chromatofocussed on Mono-P. To every 1ml of the chromatofocussed material (at 3-5mg/ml of protein) was added 2ml of 50mM phosphate buffer, pH 6.7, containing 1.5M ammonium sulfate (Buffer D). The mixture was then passed through a 0.2 $\mu$m pore diameter Acrodisc filter and loaded in multiple injections of 2ml each onto a Alkyl-Superose HR10/10 FPLC column (Pharmacia) equilibrated with Buffer D. The column was washed with Buffer D until the absorbance of the affluent at O.D. 280 returned to baseline. The column was then eluted with a 60ml linear gradient running from Buffer D into Buffer E (50mM phosphate buffer, pH 6.7) and 1 ml fractions were collected.

Figure 8:
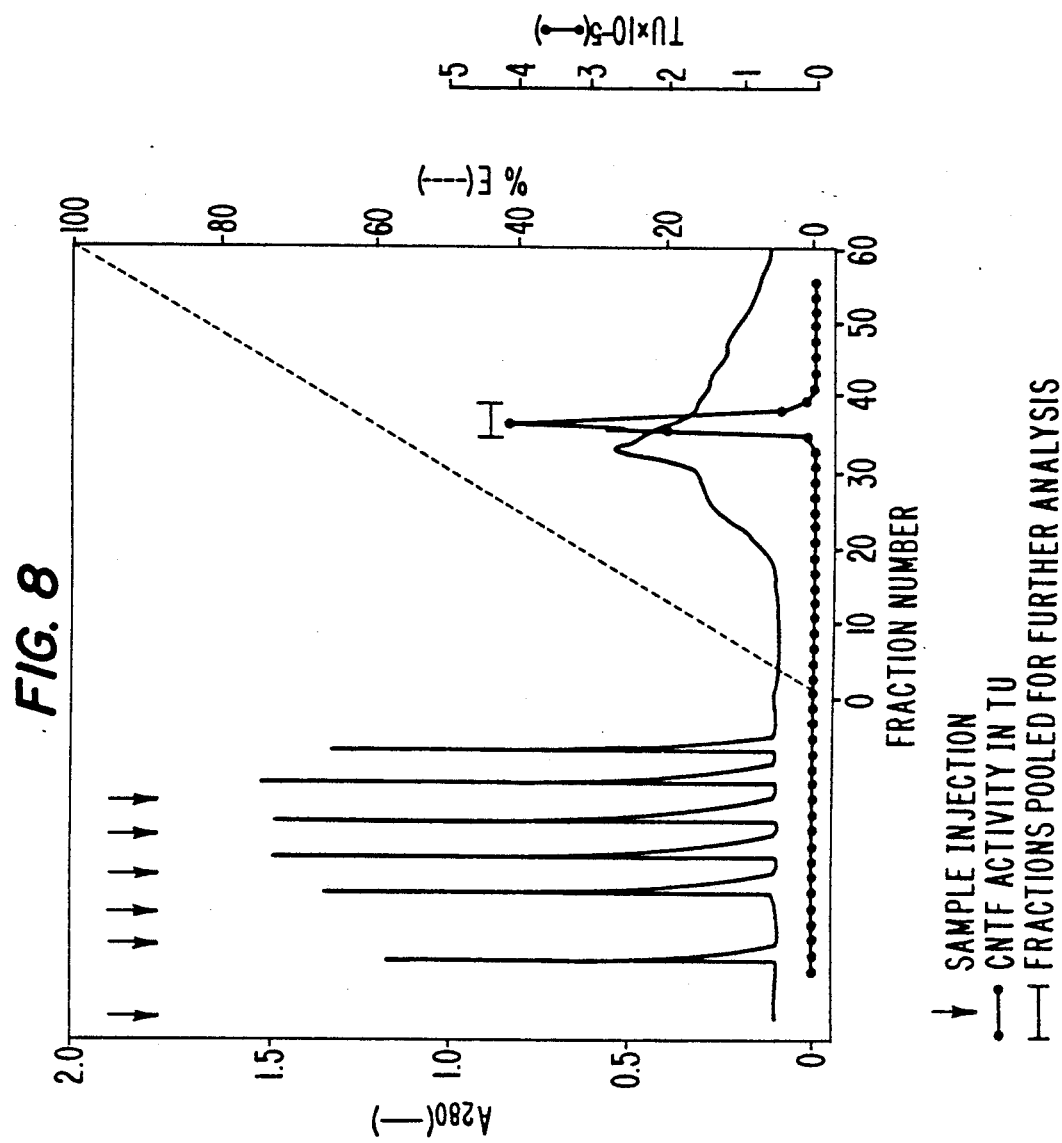
FIG. 8 depicts exemplary results of chromatography of the Mono-P chromatofocussed fraction on a alkyl-Superose FPLC-HIC column.

FIG. 8 illustrates the results of one such FPLC-HIC column run. The continuous line represents the profile of eluted protein measured by O.D. 280. Superimposed is a plot of the SN-CNTF bioactivity in each gradient fraction. The fractions containing bioactivity (indicated by the bar in FIG. 8) were pooled and concentrated in a Centricon-10 concentrator (Amicon) to 0.5ml. The sample was diluted by adding 2 ml of Buffer B to the upper reservoir and reconcentration by centrifugation to a final volume of 0.5ml. Dilution and reconcentration was repeated 2 additional times and the final concentrated sample was run on a reducing SDS-15% polyacrylamide preparative slab gel as described above, except that prior dialysis was not necessary.

Figure 9A:
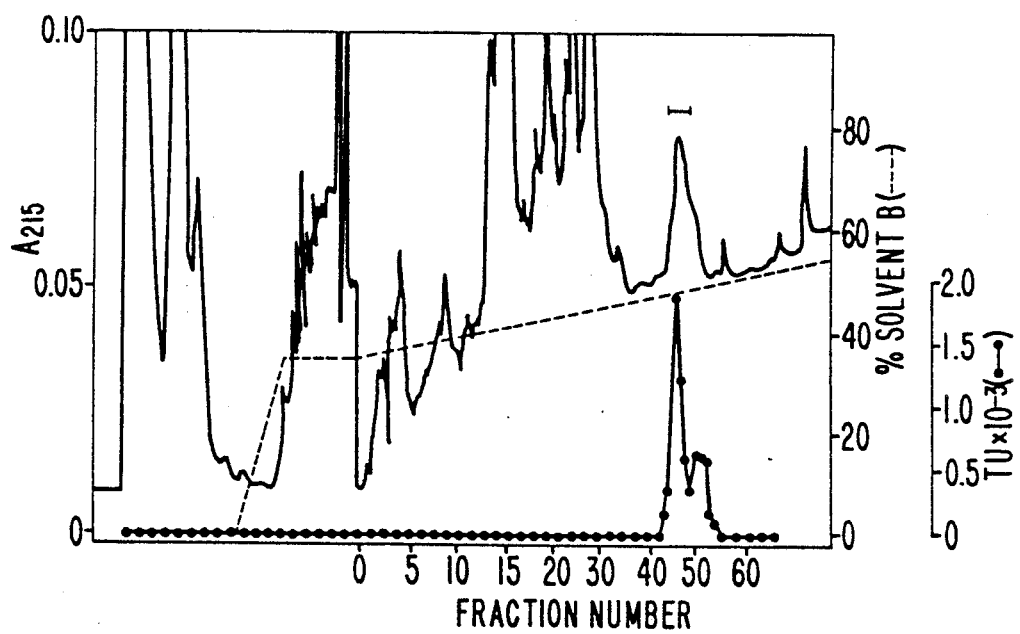
FIG. 9 depicts exemplary results of chromatography of the preparative SDS-PAGE fraction on a C8 reverse-phase HPLC column. Panel (A) illustrates the results of the original purification procedure. Panel (B) illustrates the results of the current purification procedure after addition of the two HIC chromatography steps.
Figure 9B:
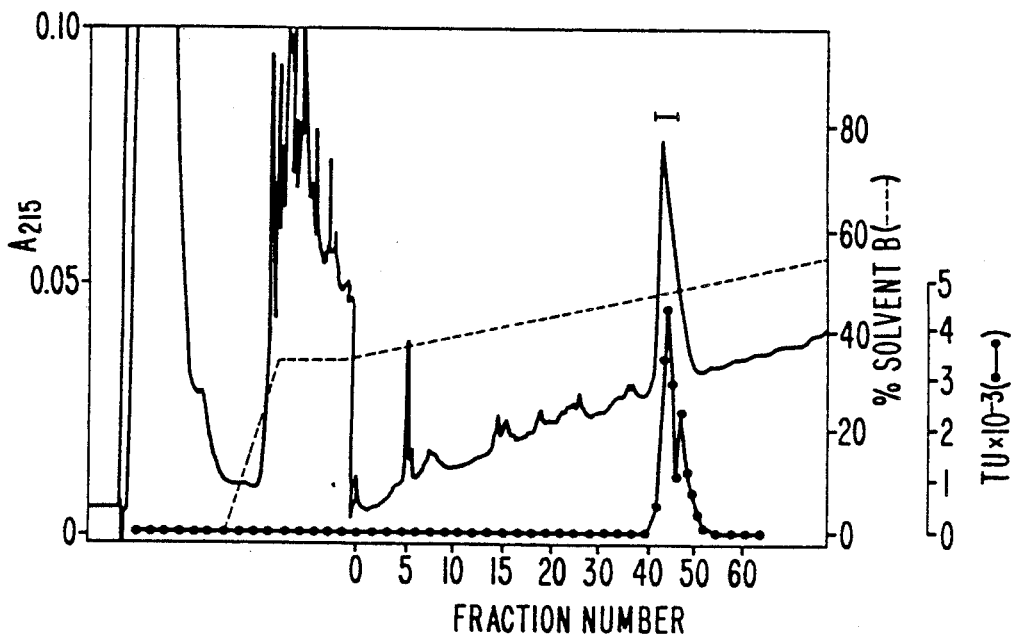

FIG. 9 compares the final purification step on reverse phase HPLC in the initial purification procedure (upper panel) and in the purification procedure after addition of the two HIC steps (lower panel). Each panel shows the profile of eluted proteins (solid line is O.D. 280 and the superimposed SN-CNTF bioactivity (line connecting x's). It is apparent from the Figure that there is much less contaminating protein present in the sample put onto reverse phase HPLC in the new purification procedure. It is important to note that the specific activity of CNTF produced by the new procedure is identical within experimental previous procedure (Table 1), indicating that the CNTF prepared by the original procedure described above was purified to homogeneity. The advantage of the new purification procedure is that 8 liters of starting material can now be processed as conveniently as 1 liter using the original procedure.

EXAMPLE 2

Sequencing of the Purified Neurotrophic Factor

Figure 5:
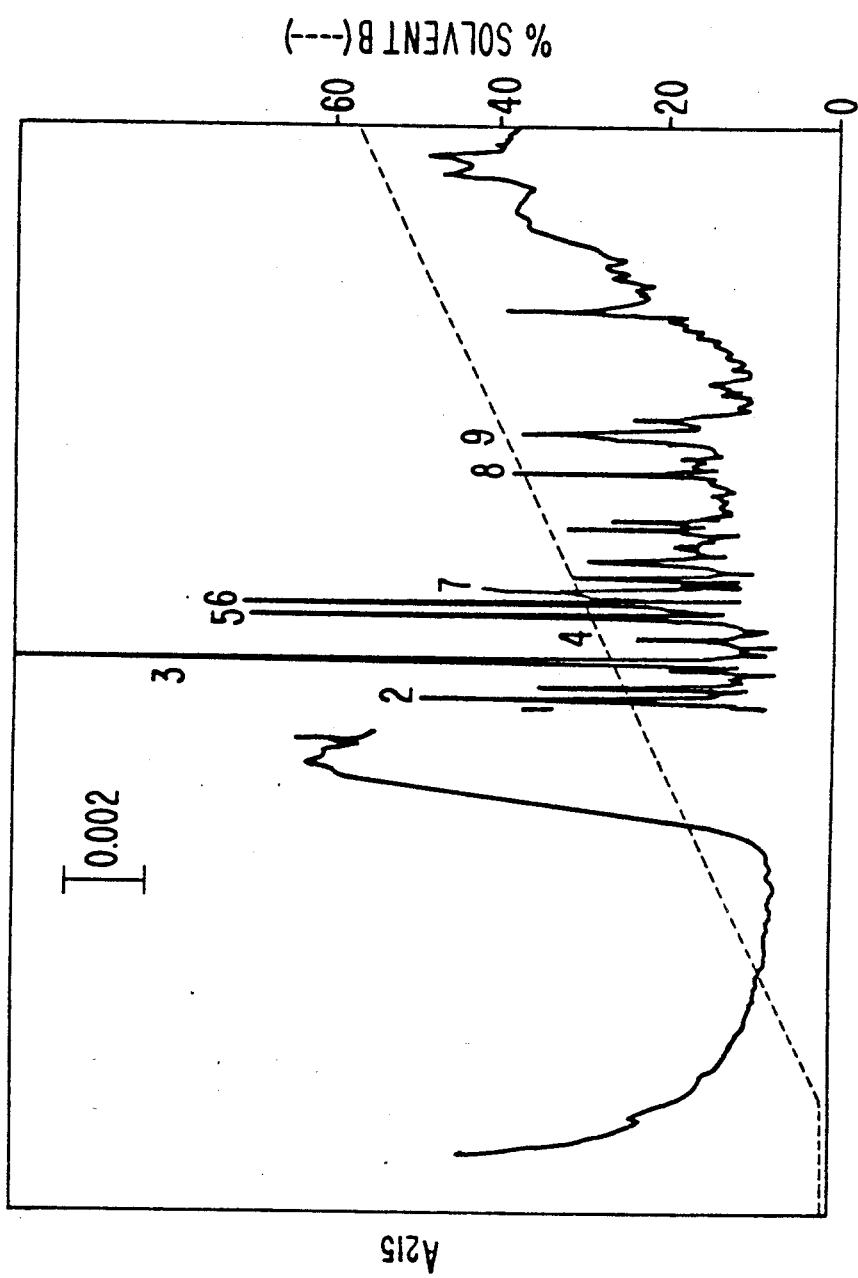
FIG. 5 depicts a profile of eluted peptides after digestion with endoprotease Asp-N.
Figure 6:
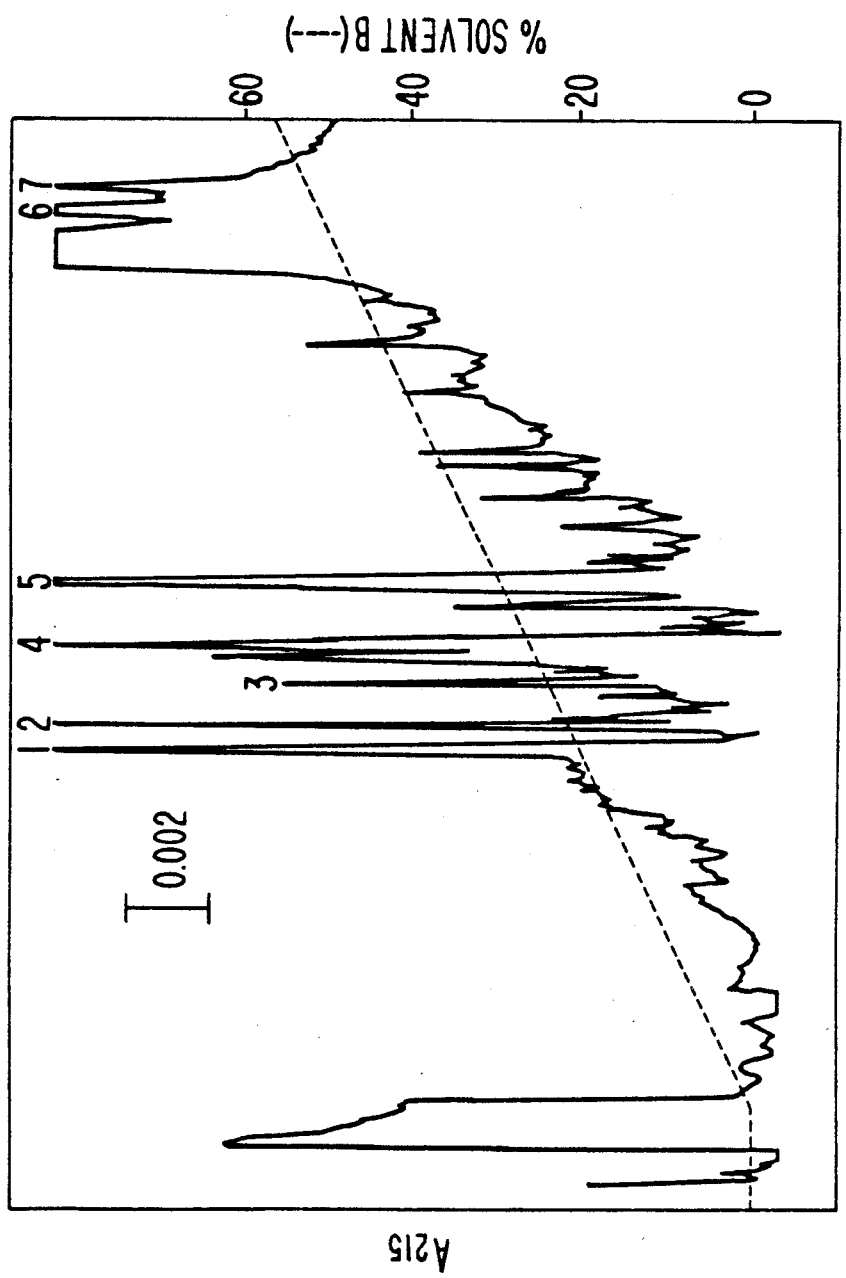
FIG. 6 depicts a profile of eluted peptides after digestion with endoprotease Lys-C.

Fractions with the peak SN-CNTF activity (#37-40, FIG. 3) were pooled and concentrated to 50 $\mu$l on a vacuum evaporator centrifuge. The concentrated sample contained 0.14% Tween 20. It was diluted with 1% ammonium bicarbonate to a final volume of 350 $\mu$l and treated with endoprotease Asp-N or endoprotease Lys-C overnight at 37° C. The mixture was concentrated to approximately 50-100 $\mu$l on a vacuum evaporator centrifuge and loaded via a 1 ml sample loop onto a narrow bore Aguapore RP-300 C8 reverse phase HPLC column (Brownlee Labs), 2.1×220mm, eluted with an $H_2O$/0.1TFA: acetonitrile/0.1% TFA gradient. Peptide containing fractions were collected manually into Eppendorf tubes based on the absorption at 215nm. FIG. 5 shows the profile of eluted peptides after digestion with endoprotease Asp-N as determined by absorbance at 215nm. FIG. 6 shows the profile of eluted peptides after digestion with endoprotease Lys-C followed by reduction and carboxymethylation. The amino acid sequence of the prominent peptides was determined using an Applied Biosystems gas phase protein sequencer.

Additional amino acid sequence has been obtained with the cleavage enzymes chymotrypsin and endoprotease Glu-C (Boehringer Mannheim Biochemicals, Indianapolis, Ind.). This additional protein sequence has allowed some of the amino acid sequences reported above to be pieced together into larger peptides from overlapping stretches of amino acids. The new amino acid sequences and those joined together with previous sequences are given below:

H—S—A—L—T—P—H—R—R—E

L—A—R—K—I—R—S—D—L—T—A—L—T—E—S—Y—V—K—H—Q—G—L—N—K—N—I—N—L—D—S—V—D—G—V—P—M—A

D—Q—Q—V—H—F—T—P—A—E—G

D—G—L—F—E—K—K—L—W—G—L—K—V—L—Q—E—L—S—H—W—T—V

D—L—R—V—I

EXAMPLE 3

Preparation of Antibodies to the Neurotroohic Factor

Antibodies that react with purified rabbit SN-CNTF will be useful for screening expression libraries in order to obtain the gene which encodes rabbit SN-CNTF. In addition, antibodies that neutralize its biological activity will be used in intact animals in order to determine the biological role of this neurotrophic factor.

In order to prepare such antibodies, synthetic peptides will be synthesized which correspond to regions of the sequence of SN-CNTF using an Applied Biosystems automated protein synthesizer. Such synthetic peptides will be covalently linked to the carrier protein keyhole limpet hemocyanin. The conjugated peptide will be injected into guinea pigs in complete Freund's adjuvant, with booster shots applied at 3 and 6 weeks in incomplete adjuvant. Serum samples will be taken from each guinea pig and used in a Western blot against purified SN-CNTF in order to determine if antibody in the serum reacts with the purified protein. Sera positive in the Western assay will be further tested for ability to neutralize the neurotrophic activity in the bioassay used for purification. Sera positive in either the Western or neutralization assay will be further purified as follows: (1) the sera will be absorbed with the carrier protein keyhole limpet hemocyanin in order to remove antibodies directed against that protein, then the sera will be retested in the above assays; (2) the IgG antibody fraction will be purified from the serum by standard procedures and retested in the above assays. Both these steps will provide a polyclonal antibody that is pure enough to be used to screen expression libraries in order to clone the messenger RNA and gene for SN-CNTF.

Antibodies were generated in rabbits to a synthetic peptide "A" corresponding to a portion of the amino acid sequence of rabbit SN-CNTF given in Example 2 (E-S-Y-V-K-H-Q-G-L-N-K-N). Methods are given in detail below in this Example. Affinity-purified antibodies against synthetic peptide A (anti-peptide-A antibodies) were prepared by passing immunized rabbit antiserum over an affinity column containing covalently-linked synthetic peptide A and then eluting bound antibodies. The unfractionated immune antiserum gave a titer of ca. $10^5$ in an ELIZA assay using peptide A coated wells; it was used at a 1:50 final dilution for Western blot analysis. The affinity-purified anti-peptide-A antibody, prepared as described below, was used in Western blot analysis at a final concentration of 80 $\mu$g/ml.

Both the anti-peptide-A antiserum and affinity-purified antibodies were demonstrated to interact with purified rabbit SN-CNTF by Western blot analysis of reducing SDS-polyacrylamide-gel electrophoresis (SDS-PAGE) of purified CNTF. Pre-immune serum from the same rabbit did not interact with SN-CNTF under these conditions. Aliquots of the peak fraction of CNTF from the final reverse-phase HPLC purification step (fraction #46, FIG. 9, panel B) were run in two separate lanes on reducing SDS-PAGE. Adjacent to each lane of purified CNTF was a lane containing molecular weight marker proteins. The gel was cut into two panels each of which contained one lane of purified CNTF and an adjacent lane of marker proteins. One of the pieces was silver-stained to localize proteins (Bio-Rad Laboratories, Richmond, Calif.) and the other was examined by Western blot analysis (Towbin et al., 1979, *Proc. Natl. Acad. Sci., U.S.A.* 76:4350) for proteins that reacted with the affinity-purified anti-peptide-A antibodies.

The left-hand panel of lanes in FIG. 10 demonstrates that the peak fraction of reverse-phase purified CNTF contains two closely-spaced protein bands that run at approximately 25,000 daltons and are separated from each other by approximately 500 daltons on reducing SDS-PAGE. When silver-stained gels are overloaded with purified CNTF, it is often not possible to resolve the two bands as in FIG. 4.

The right hand panel of lanes in FIG. 10 demonstrates that both of these bands are recognized and stained by affinity-purified anti-peptide-A antibodies. This recognition is specific since the unrelated marker proteins in the left-most lane of the right-hand pair are not recognized by the anti-peptide-A antibodies, although they are present in high concentration as demonstrated in the left-hand silver-stained lanes (FIG. 10). The pre-immune serum from this same rabbit also does not recognize the two bands of purified CNTF. These results indicate that there are at least two different forms of CNTF which differ by ca. 500 daltons in molecular weight on reducing SDS-PAGE.

To prepare anti-peptide-A antibodies, synthetic peptide A was conjugated to Keyhole Limpet Hemocyanin (KLH) to enhance its antigenicity. For conjugation, 1 mg of peptide A and 1 mg of KLH (Calbiochem, La Jolla, Calif.) in 50% glycerol were dissolved in 0.5 ml of PBS (20 mM sodium phosphate buffer, pH 7.4, M NaCl). 10% glutaraldehyde was added dropwise with mixing to a final concentration of 1%, and the reaction was allowed to stand at room temperature overnight with mixing, then diluted to 5 ml with PBS. The conjugation mixture was emulsified 1:2 with complete Freund's adjuvant and injected subcutaneously into multiple dorsal sites in two New Zealand white rabbits at ca. 100 $\mu$g peptide A per rabbit. Three weeks later, each rabbit received a booster dose of 50 $\mu$g of conjugated peptide A in incomplete Freund's adjuvant. Thereafter, similar booster injections were administered at 2-week intervals until the antiserum gave a titer of at least 100,000 in an ELIZA assay (Tainer et al., 1984, *Nature* 312:127) using peptide A-coated wells. Sera were prepared from blood collected from the ear vein 5 weeks after the initial injection and biweekly thereafter. Sera were stored at $-70°$ C.

To prepare a peptide affinity column, peptide A was covalently attached to a chromatography column matrix as follows: To 8 mg of peptide A dissolved in 0.4 ml of PBS containing 4 M guanidine hydrochloride was added 4.5 ml of 0.1 M $NaHCO_3$, pH 8.0, and 0.5 M NaCl. One gram of freeze-dried activated CH Sepharose 4B (Pharmacia) was washed and swelled in 200 ml of 1 mM HCl and immediately transferred to the solution of peptide A. The mixture was rocked overnight at 4° C. The gel was then sedimented in a clinical centrifuge and the supernatant saved for determining the amount of peptide A that became coupled to the matrix. Fifteen ml of 0.1 M TRIS buffer, pH 8.0, was added to the gel pellet and incubated at room temperature for 2 hr to block unreacted coupling groups on the gel matrix. The gel was then packed into a column (3 ml bed) and washed three times with the following buffer sequence: (1) 10 bed volumes of 0.1 M acetate buffer, pH 4.0, containing 0.5 M NaCl; (2) 0.1 M TRIS buffer, pH 8.0, containing 0.5 M NaCl. Finally, the column was equilibrated with PBS containing 0.02% sodium azide. The difference in the concentration of free amino groups was determined in the original peptide A solution and in the supernatant after conjugation, using fluorescamine (Chen et al., 1978, *Arch. Biochem. Biophys*, 189:241; Nowicki, 1979, *Anal. Letters* 12:1019). This analysis showed that 92-95% of the peptide was lost from solution and had become conjugated to the Sepharose gel matrix.

Prior to affinity purification of the anti-peptide A antibody, 8 ml of immunized rabbit serum was dialyzed overnight against 2 liters of PBS. The peptide A-Sepharose column was washed sequentially with 10 bed-volumes of each of the following: 0.1 M glycine-HCl, pH 2.5; PBS; 0.1 M triethylamine, pH 11.5; then PBS. The dialyzed serum was passed through the column three times to insure complete binding of anti-peptide-A antibodies. The column was washed with 20 bed-volumes of PBS, then eluted sequentially with 4 bed-volumes each of the following: 0.1 M glycine-HCl, pH 2.5; PBS; 0.1 M triethylamine, pH 11.5; then PBS. One ml fractions were collected. The eluates from the glycine and triethylamine washes were neutralized immediately with 1 M TRIS, pH 9 and 7, respectively, and aliquots assayed for anti-peptide A antibody with an ELIZA assay using peptide A-coated wells. The highest titer fractions (typically within 3 bed-volumes of the start of glycine and triethylamine elution) were pooled and dialyzed against PBS. After removing particulate matter by brief centrifugation, the affinity-purified antipeptide A antibody supernatant was stored at −70° C.

EXAMPLE 4

Cloning the Gene for SN-CNTF

The ultimate goal of the work to be described is to clone and express the human SN-CNTF gene in order to prepare material suitable for use in human pharmaceutical preparations. Since the peptide sequences obtained are for rabbit SN-CNTF and the rabbit and human sequences may not be identical, it is prudent to first obtain clones of the rabbit gene via hybridization with synthetic oligonucleotides based on the protein sequence and to employ the rabbit clones as hybridization probes in screens for the human gene.

Both the genomic and messenger RNA (mRNA) sequences encoding rabbit and human SN-CNTF will be obtained. The mRNA sequence will be useful for expressing the protein, whereas the genomic sequence will be essential for understanding the structure and regulation of the gene for SN-CNTF. In order to obtain these sequences, both rabbit and human genomic libraries and rabbit and human cDNA libraries made from mRNA isolated from sciatic nerves will be screened. In the process of obtaining the gene corresponding to the sequence of rabbit or human SN-CNTF, it is also possible to screen for structurally closely related genes that may represent additional members of this family of neurotrophic factors.

A. SN-CNTF Gene

To isolate the rabbit genomic sequences encoding SN-CNTF, a rabbit genomic library (Clontech) will be plated on the E.coli nm538 bacterial strain and approximately 1,000,000 recombinant clones will be screened. Regions of the protein sequence of rabbit SN-CNTF that can be represented by the fewest codons will be reverse-translated and corresponding degenerate oligonucleotide probes will be synthesized. The rabbit oligonucleotides will be labeled by kinasing according to the standard protocol of Maniatis et al. (1982, Molecular Cloning, A Laboratory Manual, Cold Spring Harbor Laboratory). The DNA kinase is obtained from U.S. Biochemical Corp. and the gamma labeled ATP is obtained from ICN. Oligonucleotides will be labeled to a specific activity of at least 1,000,000 cpm per picomole.

Upon plating of the genomic library, approximately 1 million plaques will be transferred onto duplicate nitrocellulose filters. The filters will then be processed according to the methods of Maniatis et al. (1982, ibid.) and hybridized overnight with radioactively-labeled oligonucleotide probe. The hybridization cocktail will include 6×SSCP, 2×Denhardt's, 0.05% sodium pyroophosphate, 1 mM EDTA, 0.1% SDS, 100 ug yeast tRNA (Sigma), pH 8.0. The temperature of hybridization will be several degrees below the calculated Tm of the oligonucleotide. Clones that hybridize with several probes based on different regions of the protein sequence will be plaque purified and the regions of hybridization will be sequenced by dideoxy termination method (Sanger et al., 1977, Proc. Natl. Acad. Sci. 74:5463) using Sequenase (U.S. Biochemicals Corp.) in order to identify those clones that encode the SN-CNTF protein sequence.

B. SN-CNTF mRNA Sequences

Total cellular RNA will be obtained from rabbit and human sciatic nerves. The tissue will be homogenized in a guanidinium thiocyanate/beta-mercaptoethanol solution and the RNA will be purified by sedimentation through cesium chloride gradients (Glison et. al., 1974, Biochemistry 13:2633). Polyadenylated RNA will be selected by chromatography on oligo(dT)cellulose (Avid and Leder, 1972, Proc. Natl. Acad. Sci. 69:408). Quantitative RNA blot hybridization analysis will be performed with "antisense" oligonucleotide probes to estimate the prevalence of SN-CNTF sequences in each RNA preparation and to thereby estimate the number of independent clones one would need to screen to have at least a 99% probability of obtaining CNTF clones. Sufficient doublestranded complimentary DNA will be synthesized as described by Gubler and Hoffman, 1983, Gene 25:263, and inserted into the lambda gem2 vector (Promega Biotech) according to Palazzolo and Meyerowitz, 1987, Gene 52:197.

Rabbit SN-CNTF encoding clones will be identified by hybridization of recombinant phage plaques as described above. The identities of the clones will be verified by determination of nucleotide sequences in order to determine correspondence with the entire known protein sequence. Screens of the human sciatic nerve cDNA library will be conducted with randomly primed rabbit SN-CNTF cDNA probes (Feinberg and Vogelstein, 1983, Anal. Biochem. 132:6), which is a more reliable procedure for detecting cross-species hybridization than the use of the smaller oligonucleotides used to screen the rabbit cDNA libraries.

The Polymerase Chain Reaction (PCR) (Saiki et al., 1988, Science 239:487) was used to amplify DNA fragments corresponding to rabbit CNTF amino acid sequences. Such DNA fragments were amplified from human and rabbit genomic DNA and rabbit sciatic nerve and sympathetic ganglion cDNA. The amplified DNA fragments were subcloned and sequenced using standard techniques (Maniatis et al., 1982, Molecular Cloning: A laboratory manual, Cold Sprinq Harbor, N.Y.).

The DNA fragments obtained by PCR were also used as probes to screen a rabbit sciatic nerve cDNA library and a human genomic DNA library. A positive rabbit cDNA clone and positive human genomic clones were purified and partially sequenced. The sequence of the open reading frame corresponding to the coding (mRNA equivalent) sequence for rabbit or human CNTF confirmed the sequence of the DNA fragments of the coding region obtained using PCR. The resulting coding sequences for rabbit and human CNTF are given in FIGS. 11 and 12, respectively.

Portions of the amino acid sequence obtained from rabbit SN-CNTF were reverse translated into the degenerate oligonucleotides #'s 1, 13, 7, and 12 and their complements #'s 3, 14, 8, and 17. The amino acid sequence (on top) and the location and numbering of the corresponding sense and anti-sense degenerate oligonucleotides (underneath) is given below:

Y—V—K—H—Q—G—L—N—K—N—I—N—L—D—S—V—D—G—V—P—M—A (5') *******1****** ****13**** ******7******** (3')

(3') *******3****** ****14**** ******8******** (5')

K—L—W—G—L—K—V—L—Q—E—L—S (5') *******12******* (3')

(3') *******17******* (5')

The nucleotide sequence of the sense version of each of the degenerate oligonucleotides is given below (where N corresponds to any nucleotide):

| #1   | 5' - TA(T/C) GTN AA (A/G) CA(T/C) CA(A/G) GG - 3' |
|------|---------------------------------------------------|
| #13  | 5' - AA(T/C) AA(A/G) AA(T/C) AT(A/T/C) AA (T/C) (C/T)T - 3' |
| #7   | 5' - GA(T/C) GGN GTN CCN ATG GC - 3'              |
| #12A | 5' - AA(A/G) TT(A/G) TGG GGN TT(A/G) AA - 3'      |
| #12B | 5' - AA(A/G) TT(A/G) TGG GGN CTN AA - 3'          |
| #12C | 5' - AA(A/G) CTN TGG GGN TT(A/G) AA - 3'          |
| #12D | 5' - AA(A/G) CTN TGG GGN CTN AA - 3'              |

Separate Polymerase Chain Reactions were performed using either human or rabbit genomic DNA as template and oligonucleotides #'s 1 and 8 or #'s 1 and 17 as primers, in order to amplify the corresponding regions of the human and rabbit CNTF genes. Southern blots of the reaction products (probed with radiolabeled oligonucleotide #13) revealed the existence of labeled bands ca. 66 base pairs (#'s 1 and 8) and ca. 366 base pairs (#'s 1 and 17) in size.

The same PCR reactions described above were run using cDNA prepared either from rabbit sciatic nerve or rabbit sympathetic ganglion mRNA. RNA was prepared from rabbit sciatic nerves or sympathetic ganglia and passed over an oligo-dT column to select for messenger RNA (mRNA), as described above. Complementary DNA (cDNA) was prepared with reverse transcriptase using the mRNA as template and oligo-dT as primer. When PCR was performed using either cDNA as template and either oligonucleotides #'s 1 and 8 or #'s 1 and 17 as primers, fragments were amplified which had the same sequence as those amplified from the rabbit genomic DNA (FIG. 11). This indicates that there are no intervening sequences (introns) in the protein coding region of the CNTF gene between oligonucleotides #'s 1 and 17.

An additional strategy was used to obtain more of the coding (messenger RNA equivalent) sequence for rabbit CNTF: Double-stranded cDNA was prepared using rabbit sciatic nerve mRNA as template and an oligo-dt/Not I linker adapter as primer. Subsequently, an EcoRI/XmnI-linker adapter (5'- AATT-CGAACCCCTTCG-3') was added to the 5'-end of the double-stranded blunt-end ligation (Maniatis et al., ibid.). The Polymerase Chain Reaction was performed using this cDNA as a template and oligonucleotides #8 and EcoRI/XmnI-linker-adapter as primers. A Southern blot of the reaction products (probed with radiolabeled oligonucleotide #13) revealed the existence of a labeled band approximately 200 base pairs in size.

To obtain cDNA clones for rabbit CNTF, a cDNA library was prepared from rabbit sciatic nerve poly(A)+ mRNA by the methods described above, except for the use of a lambda gt10 vector (Stratigene) in place of lambda gem2. Approximately $4 \times 10^6$ plaques of this library were screened using a probe prepared by randomly labeling an M13 subclone of a PCR fragment obtained from rabbit sympathic ganglion cDNA as template and oligos #8 and Eco RI/Xmn I liker adapter as primers (see above). The single primary positive was plaque purified through a tertiary screen. Upon digestion with Eco RI, the DNA from this clone yielded three fragments in addition to the lambda arms: ca. 2.0, 1.5, and 0.6 kb in length. By Southern blot analysis the 1.5 kb fragment was shown to hybridize to other CNTF-specific oligonucloetides and PCR fragments referred to above. The DNA sequence of this 1.5 kb cDNA fragment established that it contained the entire coding sequence for rabbit CNTF (FIG. 11).

To obtain genomic DNA clones for human CNTF, approximately $3 \times 10^6$ plaques of a human genomic DNA library in vector lambda EMBL3 were screened using a probe prepared by randomly labeling an M13 subclone of a PCR fragment obtained from human genomic DNA as template and oligos #1 and #17 as primers (see above). Six of the primary positives were plaque purified by subsequent screening and found to hybridize to additional CNTF-specific oligonucleotides and PCR fragments. A 0.6 kb Bam HI restriction fragment from one of the clones hybridizing to oligo #13 was subcloned into Bam HI-cut M13mp19 and sequenced.

The DNA sequences of the fragments obtained by PCR from rabbit material from the rabbit cDNA clone were combined based on regions of overlapping sequence to give the cloning (mRNA equivalent) sequence for rabbit SN-CNTF presented in FIG. 11. The DNA sequences of the fragments obtained by PCR from human genomic DNA and from human genomic clones were combined based on regions of overlapping sequence to give the coding sequence for human SN-CNTF presented in FIG. 12. The rabbit and human nucleic acid sequences for CNTF are ca. 89% identical (FIG. 12), indicating that the rabbit and human sequences are from homologous genes encoding CNTF. As shown in FIG. 11, parts of the nucleic acid sequence for rabbit CNTF are confirmed by the amino acid sequences obtained from purified SN-CNTF and reported in earlier examples.

The Polymerase Chain Reaction was performed using the templates and primers described above. The program for the reactions was as follows: denaturation cycle, 1 min. at 95° C.; annealing cycle, 1.5 min. at 40°0 C.; and extension cycle, 4 min. at 72° C. The reaction was performed for 30 cycles. The reaction products were electrophoresed through 2% agarose gels and transferred onto Zeta-Bind membranes (BioRad, Richmond, Calif.) for Southern blotting. In order to identify the amplified portions of the CNTF coding sequence, the Southern blots were probed with a radiolabeled oligonucleotide #13, known from the CNTF protein sequence to lie between the oligonucleotides used to prime the reaction. The labeled bands obtained after Southern blotting were cut from the original gels and prepared for cloning by repairing the ends with Klenow fragment of the DNA polymerase (New England Biolabs, Beverly, Mass.) in the presence of all four dNTPs and kinasing the DNA by with T4 polynucleotide kinase (U.S. Biochemical Corp., Cleveland, Ohio) and ATP. The appropriate DNA pieces were then subcloned into M13mp10 SmaI-cut vector (dephosphorylated; commercially available from Amersham Corp., Arlington Heights, Ill.). The recombinant phages containing the fragment of interest were identified by Benton & Davis (1977, Science 196:180) screening procedure using radiolabeled oligonucleotide #13 as a probe. These recombinant clones were grown up to obtain sufficient quantities of single-stranded DNA for sequencing and were then sequenced by the dideoxy chain termination method (Sanger, et al., ibid.)

The hybridization conditions when long, randomly-labeled DNA probes were used were 5×SSCP, 2×Denhardt's, 2mM EDTA, 0.05% sodium pyrophosphate, 0.1% sodium dodecyl sulfate (SDS), 250 µg/ml of herring sperm DNA (non-specific competitor), pH 8.0. Hybridization was carried out at 65° C. and blots or filters were washed at 65° C. in 0.1×SSCP and 0.1% SDS. The hybridization conditions for shorter, oligonucleotide probes were 6×SSCP, 2×Denhardt's, 2 mM EDTA, 0.05% sodium pyrophosphate, 0.1 SDS, 100 µg/ml yeast tRNA (non-specific competitor), pH 8.0. The temperature of hybridization and the conditions for washing blots and filters were individually adjusted for the GC content of each oligonucleotide (Maniatis et al., ibid.).

EXAMPLE 5

Expression of Genes Encoding SN-CNTF in Animal Cells

Animal-cell expression of SN-CNTF requires the following steps:
  a. Construction of an expression vector;
  b. Choice of a host cell line;
  c. Introduction of the expression vector into host cells; and
  d. Manipulation of recombinant host cells to increase expression levels of SN-CNTF.

(a) SN-CNTF expression vectors designed for use in animal cells can be of several types including strong constitutive expression constructs, inducible gene constructs, as well as those designed for expression in particular cell types. In all cases, promoters and other gene regulatory regions such as enhancers (inducible or not) and polyadenylation signals are placed in the appropriate location in relation to the cDNA sequences in plasmid-based vectors. Two examples of such constructs follow: (1) A construct using a strong constitutive promoter region should be made using the simian virus 40 (SV40) gene control signals in an arrangement such as that found in the plasmid pSV2CAT as described by Gorman et al. in Mol. Cel. Biol. 2: 1044–1051, 1982, specifically incorporated herein by reference. This plasmid should be manipulated in such a way as to substitute the SN-CNTF cDNA for the chloramphenicol acetyltransferase (CAT) coding sequences using standard molecular biological techniques (Maniatis et al., supra). (2) An inducible gene construct should be made utilizing the plasmid PMK which contains the mouse metallothionein (MT-1) promoter region (Brinster et al., Cell 27:228-231, 1981). This plasmid can be used as a starting material and should be manipulated to yield a metal-inducible gene construct.

(b) A number of animal cell lines should be used to express SN-CNTF using the vectors described above to produce active protein. Two potential cell lines that have been well characterized for their ability to promote foreign gene expression are mouse Ltk⁻and Chinese hamster ovary (CHO) dhfr⁻cells, although expression of SN-CNTF is not limited to these cell lines.

Animal cell lines that can be used for expression in addition to those mentioned above include the monkey kidney cell COS-7, which is useful for transient expression, and the human embryonic kidney cell 293.

(c) Vector DNA should be introduced into these cell lines using any of a number of gene-transfer techniques. The method employed here involves the calcium phosphate-DNA precipitation technique described by S. L. Graham and A. S. van der Eb (Virology 52:456–467, 1973) in which the expression vector for SN-CNTF is co-precipitated with a second expression vector encoding a selectable marker. In the case of Ltk⁻cell transfection, the selectable marker is a thymidine kinase gene and the selection is as described by Wigler et al. in Cell 16:L777–785, 1979 and in the case of CHO dhfr⁻cells, the selectable marker is dihydrofolate reductase (DHFR) whose selection is as described by Ringold et al. in J. Mol. Appl. Genet. 1:165–175, 1981.

(d) Cells that express the SN-CNTF gene constructs should then be grown under conditions that will increase the levels of production of SN-CNTF. Cells carrying the metallothionein promoter constructs can now be grown in the presence of heavy metals such as cadmium which will lead to a 5 fold increased utilization of the MT-1 promoter (Mayo et al., Cell 29:99–108) subsequently leading to a comparable increase in SN-CNTF protein levels. Cells containing SN-CNTF expression vectors (either SV40or MT-1-based) along with a DHFR expression vector can be taken through the gene amplification protocol described by Ringold et al. in J. Mol. Apl. Genet. 1:165:175, 1981, using methotrexate, a competitive antagonist of DHFR. This leads to more copies of the DHFR genes present in the cells and, concomitantly, increased copies of the SN-CNTF genes which, in turn, can lead to more SNCNTF protein being produced by the cells.

Figure 13:
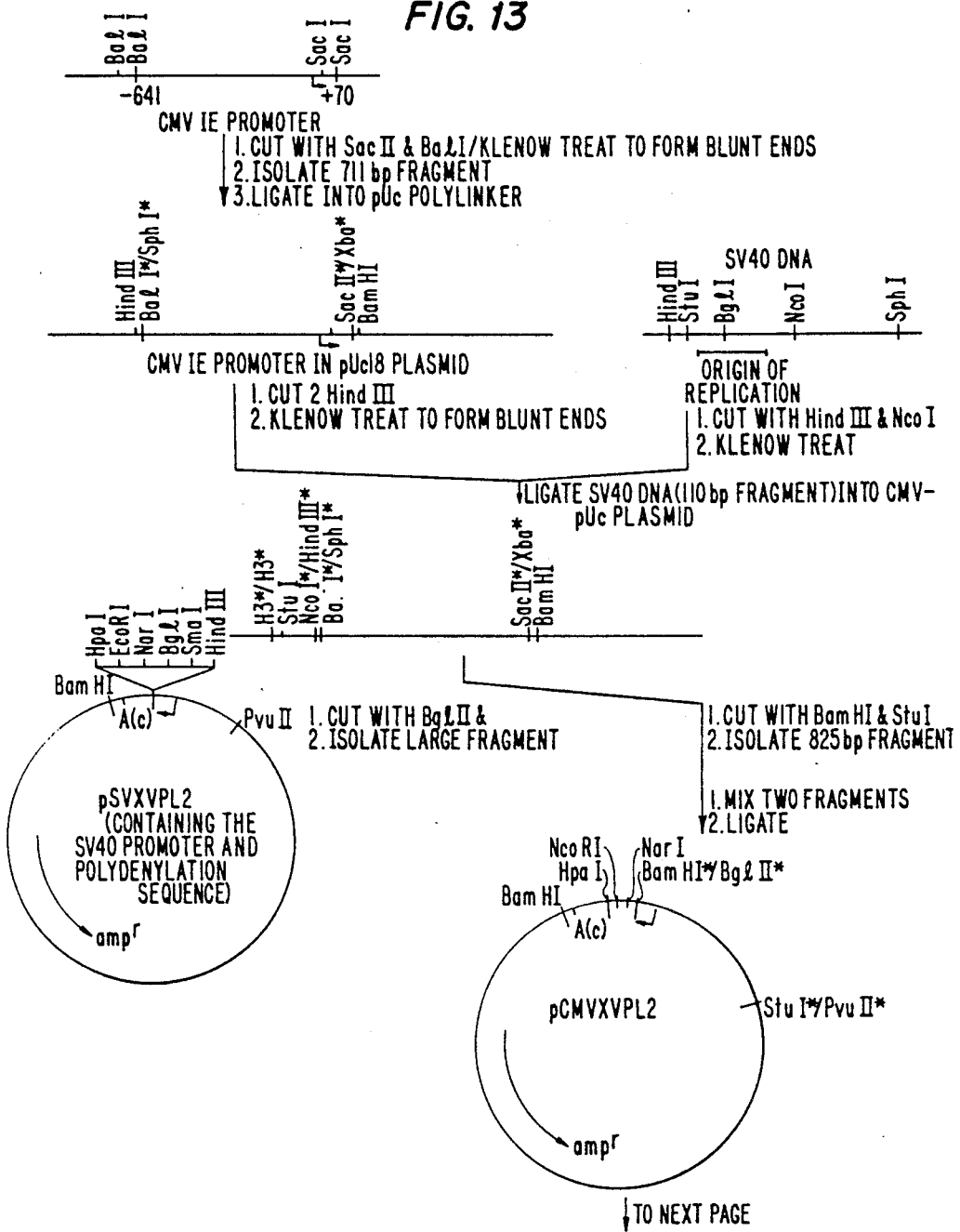
FIG. 13 depicts the construction of the pCMVXVPL2 expression vector.

An additional expression vector, pCMVXVPL2, was utilized to express the coding sequence for rabbit CNTF transiently in COS-7 cells. This plasmid vector contains the cytomegalovirus (CMV) immediate early promoter and enhancer as described by Boshart et al. (Cell 41:521–530, 1985). This plasmid can be constructed as shown in FIG. 13. The polyadenylation signal is provided by simian virus 40 (SV40) sequences (map coordinates 2589–2452; see Reddy et al., Science 200:494–502, 1978). The SV40 origin of replication is included in this plasmid to facilitate its use in COS cells for transient expression assays.

Rabbit SN-CNTF was transiently expressed in COS-7 cells as follows: The 1.5 kb Eco RI restriction fragment of a rabbit sciatic nerve cDNA clone containing the entire coding region for rabbit SN-CNTF (Example 4) was subcloned into the Eco RI-cut expression vector pCMVXVPL2. A single clone was selected which gave restriction fragments, after digestion with Sac I and Bam HI, that were of the size predicted for insertion of the 1.5 kb fragment into the vector in the correct orientation for CNTF expression. Plasmid DNA from this construct was prepared by the method of alkaline lysis followed by CsCl density centrifugation (Maniatis et al., ibid.). This DNA was transfected into COS-7 cells by the method of Sompayrac and Danna (Proc. Natl. Acad. Sci., U.S.A. 78:7575–7578, 1981). As a control, equivalent COS cell cultures were transfected with plasmid vector DNA with no insert.

Forty-eight hours after transfection, the overlying medium and cell pellets were harvested. Cell pellets were extracted by brief sonication on ice in 20 mM sodium phosphate, pH 6.7 containing 1 mM EDTA, 0.1mM PMSF, and 0.1 μM pepstatin. Serial dilutions of both the cell extract and the overlying medium from each culture were assayed for activity in the ciliary ganglion survival assay.

The cell extracts from cultures transfected with vector containing the CNTF cDNA fragment had a titer of ca. 15,000 TU/ml in the bioassay and approximately 50 ng/ml of CNTF as determined by Western blot analysis. Neither the cell extracts from cultures transfected with vector alone nor the overlying medium from any cultures displayed any detectable bioactivity or CNTF protein by Western blot analysis. This result clearly demonstrates that the CNTF cDNA we have cloned encodes a protein with the anticipated bioactivity of authentic SN-CNTF.

EXAMPLE 6

Purification of SN-CNTF from Recombinant Animal Cells

Since SN-CNTF is expected to be synthesized by cells like the natural material, it is anticipated that the methods described above for purification of the natural protein will allow similar purification and characterization of the recombinant protein.

It will be apparent to those skilled in the art that various modifications and variations can be made in the processes and products of the present invention. Thus, it is intended that the present invention cover the modifications and variations of this invention provided they come within the scope of the appended claims and their equivalents. Also, the term SN-CNTF is intended to encompass all origins of species, unless the term is immediately preceded by a specific origin of species.

What is claimed is:

1. The nucleic acid sequence encoding rabbit SN-CNTF as set forth in FIG. 11.
2. The nucleic acid sequence encoding human CNTF as set forth in FIG. 12.
3. A recombinant expression system for producing biologically active SN-CNTF comprised of an animal cell transfected with a vector containing a nucleic acid sequence encoding for SN-CNTF.

* * * * *

UNITED STATES PATENT AND TRADEMARK OFFICE
CERTIFICATE OF CORRECTION

PATENT NO. : 4,997,929  
DATED : March 5, 1991  
INVENTOR(S) : Collins et al.

Page 1 of 2

It is certified that error appears in the above-identified patent and that said Letters Patent is hereby corrected as shown below:

Drawings,  
Drawing sheet, consisting of Fig. 12, should be deleted and substituted with the following:

*FIG. 12*

```
                                             G              TG
                                    TAA GGG ATG GCT TTC ACA GAG
                                        met ala phe thr glu
                                                        met
         G A                    C       G              T A C
CAT TCA CCG CTG ACC CCT CAC CGT CGG GAC CTC TGT AGC CGC TCT ATC TGG
his ser pro leu thr pro his arg arg asp leu cys ser arg ser ile trp
        ala                             glu                 thr
        G                               C                   T   C
CTA GCA AGG AAG ATT CGT TCA GAC CTG ACT GCT CTT ACG GAA TCC TAT GTG
leu ala arg lys ile arg ser asp leu thr ala leu thr glu ser tyr val
                                        T              A G A
AAG CAT CAG GGC CTG AAC AAG AAC ATC AAC CTG GAC TCT GCG GAT GGG ATG
lys his gln gly leu asn lys asn ile asn leu asp ser ala asp gly met
                                                   val          val
    A                                   T
CCA GTG GCA AGC ACT GAT CAG TGG AGT GAG CTG ACC GAG GCA GAG CGA CTC
pro val ala ser thr asp gln trp ser glu leu thr glu ala glu arg leu
    met
       C              G          A  A                           T
CAA GAG AAC CTT CAA GCT TAT CGT ACC TTC CAT GTT TTG TTG GCC AGG CTC
gln glu asn leu gln ala tyr arg thr phe his val leu leu ala arg leu
                                                ile met
                                        G T
TTA GAA GAC CAG CAG GTG CAT TTT ACC CCA ACC GAA GGT GAC TTC CAT CAA
leu glu asp gln gln val his phe thr pro thr glu gly asp phe his gln
                                                ala
            T A        T           C  T
GCT ATA CAT ACC CTT CTT CTC CAA GTC GCT GCC TTT GCA TAC CAG ATA GAG
ala ile his thr leu leu leu gln val ala ala phe ala tyr gln ile glu
```

UNITED STATES PATENT AND TRADEMARK OFFICE
CERTIFICATE OF CORRECTION

PATENT NO. : 4,997,929
DATED : March 5, 1991
INVENTOR(S) : Collins et al.

It is certified that error appears in the above-identified patent and that said Letters Patent is hereby corrected as shown below:

FIG. 12 (CONTINUED)

```
          G G   G T         GT  T       T  CC   A    T
GAG TTA ATG ATA CTC CTG GAA TAC AAG ATC CCC CGC AAT GAG GCT GAT GGG
glu leu met ile leu leu glu tyr lys ile pro arg asn glu ala asp gly
            val                 cys asn         pro lys asp
 CA    G C  ---             GT   A
ATG CCT ATT AAT GTT GGA GAT GGT GGT CTC TTT GAG AAG AAG CTG TGG GGC
met pro ile asn val gly asp gly gly leu phe glu lys lys leu trp gly
        val --- ile     gly asp
  G           A   A             C           G   A         T
CTA AAG GTG CTG CAG GAG CTT TCA CAG TGG ACA GTA AGG TCC ATC CAT GAC
leu lys val leu gln glu leu ser gln trp thr val arg ser ile his asp
                              ,his
        G             G .       A     A             A
CTT CGT TTC ATT TCT TCT CAT CAG ACT GGG ATC CCA GCA CGT GGG AGC CAT
leu arg phe ile ser ser his gln thr gly ile pro ala arg gly ser his
        val           cys                           his
            G           G
TAT ATT GCT AAC AAC AAG AAA ATG TAG
tyr ile ala asn asn lys lys met
                asp     glu
```

Signed and Sealed this

Twenty-eighth Day of May, 2002

Attest:

JAMES E. ROGAN
*Attesting Officer*    *Director of the United States Patent and Trademark Office*